US012758663B2

(12) United States Patent
Barrios Sierra et al.

(10) Patent No.: US 12,758,663 B2
(45) Date of Patent: Oct. 13, 2026

(54) ULTRAVIOLET DISINFECTOR AND RELATED METHODS FOR DISINFECTING ARTICLES

(71) Applicant: Anram Holdings, Mississauga (CA)

(72) Inventors: Jose Miguel Barrios Sierra, Toronto (CA); Romil Hitenbhai Dalvadi, Brampton (CA)

(73) Assignee: Pulse RX Disinfection Corp., Oakville (CA)

( * ) Notice: Subject to any disclaimer, the term of this patent is extended or adjusted under 35 U.S.C. 154(b) by 1036 days.

(21) Appl. No.: 17/390,081

(22) Filed: Jul. 30, 2021

(65) Prior Publication Data

US 2022/0031881 A1 Feb. 3, 2022

Related U.S. Application Data

(60) Provisional application No. 63/059,899, filed on Jul. 31, 2020.

(51) Int. Cl.
*A61L 2/10* (2026.01)
*A61L 2/24* (2006.01)
(Continued)

(52) U.S. Cl.
CPC .................. *A61L 2/10* (2013.01); *A61L 2/24* (2013.01); *A61L 2/26* (2013.01); *A61L 2103/00* (2026.01)

(58) Field of Classification Search
CPC ..... A61L 2/10; A61L 2/24; A61L 2/26; A61L 2202/20; A61L 2202/122; A61L 2202/14
See application file for complete search history.

(56) References Cited

U.S. PATENT DOCUMENTS

| | | |
|---|---|---|
| 9,254,342 B2 | 2/2016 | Engelhardt et al. |
| 9,433,694 B1 | 9/2016 | Hsu |

(Continued)

FOREIGN PATENT DOCUMENTS

| | | |
|---|---|---|
| CN | 202342503 U | 7/2012 |
| CN | 212233703 U | 12/2020 |

(Continued)

OTHER PUBLICATIONS

International Search Report & Written Opinion dated Nov. 1, 2021; WIPO Application No. PCT/CA2021/051076.

*Primary Examiner* — Brendan A Hensel
(74) *Attorney, Agent, or Firm* — Rowand LLP

(57) ABSTRACT

Embodiments of the present disclosure provide an apparatus and a method for disinfecting an article. The method includes providing a disinfection container inside a cabinet having an opening. The disinfection container includes an ultraviolet (UV) source, a tray moveable between a first position outside the cabinet for placement and retrieval of an article and a second position within the disinfection container for article disinfection, and a barrier. The method also includes moving the tray (i) outwards from the disinfection container to pivot the barrier away from the opening for extending the tray to the first position and (ii) towards the second position to pivot the barrier towards the opening for blocking the opening to prevent access to the tray in the second position through the opening, and projecting UV light from the UV source on to the article in the second position until a disinfection cycle is complete.

20 Claims, 15 Drawing Sheets

(51) Int. Cl.

| | |
|---|---|
| ***A61L 2/26*** | (2006.01) |
| ***A61L 103/00*** | (2026.01) |

(56) References Cited

U.S. PATENT DOCUMENTS

| | | | | |
|---|---|---|---|---|
| 10,772,979 | B2 | 9/2020 | Baranov et al. | |
| 11,191,857 | B2 * | 12/2021 | Pangan, Jr. | A61L 2/10 |
| 2009/0257912 | A1 | 10/2009 | Lane et al. | |
| 2009/0322190 | A1 | 12/2009 | Kitagawa et al. | |
| 2014/0060095 | A1 * | 3/2014 | Shur | A61L 2/10<br>250/455.11 |
| 2018/0117192 | A1 * | 5/2018 | Baranov | A61L 2/10 |
| 2018/0193502 | A1 * | 7/2018 | Ufkes | A61B 90/70 |
| 2018/0221520 | A1 * | 8/2018 | Nguyen | A61L 2/24 |
| 2018/0357385 | A1 * | 12/2018 | LaPorte | A61L 2/08 |
| 2020/0030470 | A1 * | 1/2020 | Mauzerall | A61L 2/07 |
| 2021/0308296 | A1 * | 10/2021 | Cook | A47B 49/008 |

FOREIGN PATENT DOCUMENTS

| | | | |
|---|---|---|---|
| CN | 213444110 | U | 6/2021 |
| CN | 213466129 | U | 6/2021 |
| WO | 2016170511 | | 10/2016 |
| WO | 2019072205 | | 4/2018 |
| WO | 2020102896 | | 5/2020 |

* cited by examiner

ULTRAVIOLET DISINFECTOR AND RELATED METHODS FOR DISINFECTING ARTICLES

TECHNICAL FIELD

The subject matter generally relates to ultraviolet devices and particularly relates to an ultraviolet disinfector and related methods for disinfecting articles.

BACKGROUND

Surfaces of portable articles, such as mobile phones and wallets, tend to harbour various harmful pathogens such as bacteria and viruses. Different types of devices are known to disinfect such articles. Most conventional devices use ultraviolet (UV) light for disinfection. Such a UV-based disinfecting device typically requires a user to manually operate a door/cover for placing a contaminated article (e.g., mobile phone) directly into a disinfection chamber within the device. In the disinfection chamber, the article is typically supported on a surface surrounded by UV bulbs emitting the UV light for disinfection. Such direct access to the disinfection chamber for placing the article increases the risk of accidental damage to sensitive portions thereof, such as reflectors and bulbs, by the user. Moreover, the door/cover can catch pathogens upon coming in contact with the user, thereby risking transmission of pathogens to other users and raising a device upkeep cost.

SUMMARY

One embodiment of the present disclosure includes an apparatus for disinfecting an article. The apparatus includes a disinfection container inside a cabinet having an opening, a tray, a barrier, a controller, and an ultraviolet (UV) source. The tray may be movably attached to the disinfection container, where the tray is moveable between a first position outside the cabinet for placement and retrieval of an article in the tray and a second position within the disinfection container for disinfection of the article. The barrier may be pivotally coupled to the tray. The barrier may be moved by the tray and configured to pivot (i) away from the opening based on the tray being moved outwards from the disinfection container, for extending the tray through the opening to the first position, and (ii) towards the opening based on the tray being moved towards the second position, for gradually blocking the opening to prevent access to the tray in the second position through the opening. The controller may be configured for moving the tray, via an actuator, to (i) the first position based on one of a first sensor input and completion of a disinfection cycle and (ii) the second position based on one of a second sensor input and a set duration. The UV source may be attached to the disinfection container for projecting UV light on to the article in the second position of the tray until the disinfection cycle is complete.

Another embodiment of the present disclosure includes a method of disinfecting an article. The method includes providing a disinfection container inside a cabinet having an opening. The disinfection container includes an ultraviolet (UV) source, a tray moveable between a first position outside the cabinet for placement and retrieval of an article in the tray and a second position within the disinfection container for disinfection of the article, and a barrier pivotally coupled to the tray. The method also includes moving the tray by a controller via an actuator for driving the barrier, where the tray moving (i) outwards from the disinfection container pivots the barrier away from the opening for extending the tray to the first position via the opening and (ii) towards the second position pivots the barrier towards the opening for gradually blocking the opening to prevent access to the tray in the second position through the opening. The tray is moved to (i) the first position based on one of a first sensor input and completion of a disinfection cycle and (ii) the second position based on one of a second sensor input and a set duration. Further, the method includes projecting UV light from the UV source on to the article in the second position of the tray until the disinfection cycle is complete.

One aspect of the present disclosure includes the barrier being configured to pivot (i) upwards based on the tray being moved outwards from the disinfection container and (ii) downwards based on the tray being moved towards to the second position.

Another aspect of the present disclosure includes the tray including a base for supporting the article and walls surrounding the base, where the base is optically permeable to the UV light and the walls include reflectors.

Yet another aspect of the present disclosure includes the disinfection container including a top plate, a bottom plate, side plates connected therebetween, and an open end aligned with the opening, such that the tray may be movably attached to the side plates, where the tray may be configured to move in and out of the disinfection container through the open end.

A still another aspect of the present disclosure includes each of the top plate and the bottom plate including an inner surface proximate to the tray, where the inner surface includes a reflector.

A further aspect of the present disclosure includes the UV source being attached to one of the side plates, where the UV source may be positioned between the tray and one of the top plate and the bottom plate.

Another aspect of the present disclosure includes the UV source being adapted to project pulsed UV light.

Yet another aspect of the present disclosure includes an additional UV source for projecting UV light towards the tray such that the UV source and the additional UV source may be triggered alternately by the controller to collectively emit UV light in a pulsed manner on to the article.

A still another aspect of the present disclosure includes the disinfection container being distinct from the cabinet.

A further aspect of the present disclosure includes the disinfection container being removable from the cabinet.

Another aspect of the present disclosure includes a mobile body supporting the cabinet and the disinfection container.

Yet another aspect of the present disclosure includes a proximity sensor providing the first sensor input and the second sensor input, where the proximity sensor may be located along an outer surface of the cabinet.

A further aspect of the present disclosure includes the barrier being configured to pivot within the cabinet.

The above summary of exemplary embodiments is not intended to describe each disclosed embodiment or every implementation of the present disclosure. Other and further aspects and features of the disclosure would be evident from reading the following detailed description of the embodiments, which are intended to illustrate, not limit, the present disclosure.

BRIEF DESCRIPTION OF THE DRAWINGS

The illustrated embodiments of the subject matter will be best understood by reference to the drawings, wherein like parts are designated by like numerals throughout. The following description is intended only by way of example, and simply illustrates certain selected embodiments of devices, systems, and processes that are consistent with the subject matter as claimed herein.

DETAILED DESCRIPTION

The following detailed description is provided with reference to the drawings herein. Exemplary embodiments are provided as illustrative examples so as to enable those skilled in the art to practice the disclosure. It will be appreciated that further variations of the concepts and embodiments disclosed herein can be contemplated. The examples of the present disclosure described herein may be used together in different combinations. In the following description, details are set forth in order to provide an understanding of the present disclosure. It will be readily apparent, however, that the present disclosure may be practiced without limitation to all these details. Also, throughout the present disclosure, the terms "a" and "an" are intended to denote at least one of a particular element. The terms "a" and "an" may also denote more than one of a particular element. As used herein, the term "includes" means includes but not limited to, the term "including" means including but not limited to. The term "based on" means based at least in part on, the term "based upon" means based at least in part upon, and the term "such as" means such as but not limited to. The term "approximately" means a variation of +/−5% in a stated number or a value of a stated parameter. Further, in the present disclosure, an embodiment showing a singular component should not be considered limiting; rather, the present disclosure is intended to encompass other embodiments including a plurality of the same or similar component, and vice-versa, unless explicitly stated otherwise herein. The present disclosure also encompasses present and future known equivalents of the components referred to herein.

Figure 1:
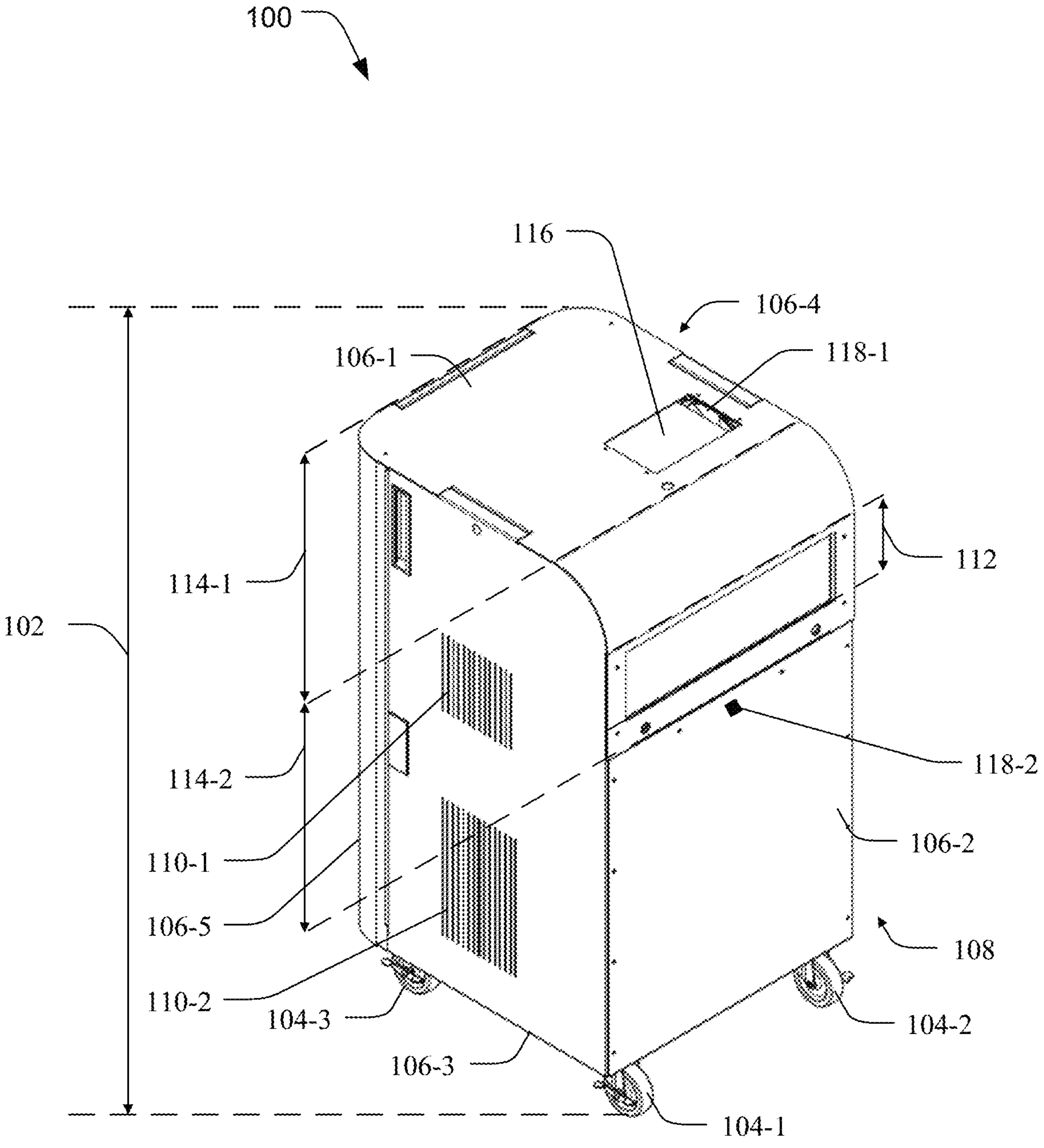
FIG. 1 is a front isometric view of an exemplary ultraviolet (UV) disinfector, according to an embodiment of the present disclosure.

FIG. 1 is a front isometric view of an exemplary ultraviolet (UV) disinfector 100, according to a first embodiment of the present disclosure. The UV disinfector 100 (or simply, disinfector 100) may represent a variety of devices and apparatuses including a disinfection chamber configured to emit or facilitate emission of a germicide for disinfecting articles received within such chamber. The germicide may include UV light alone or in combination with any other suitable types of energies or complementing agents for disinfecting surfaces of the articles. Examples of such energies may include, but are not limited to, radio, microwave, x-ray, infrared, visible, or any other specific wavelength or group of wavelengths in the electromagnetic spectrum. On the other hand, examples of such complementing agents may include, but are not limited to, chemical agents (e.g., alcohols, aldehydes, oxidizing agents, naturally occurring or modified compounds, etc.), physical agents (e.g., heat, pressure, vibration, sound, radiation, plasma, electricity, etc.), and biological agents (e.g., living organisms, plants or plant products, assistive-pathogens, organic residues, etc.) for catalyzing or effecting surface disinfection. Examples of such articles may include, but are not limited to, electronic articles (e.g., mobile phones, tablet computers, headsets, pen drives, watches, electronic reading devices, navigation devices, etc.) and non-electronic articles (e.g., pens, facial masks, gloves, jewellery, storage bins, etc.).

The disinfector 100 may be operable to communicate with a computing device (e.g., a desktop PC, a personal digital assistant (PDA), servers, mobile computing devices such as mobile phones and laptops, etc.), and internet appliances over a wired or wireless network. Embodiments of the disinfector 100 may also include a variety of known, related art, or later developed interface(s), including software interfaces (e.g., an application programming interface, a graphical user interface, etc.); hardware interfaces (e.g., cables, cable connectors, a keyboard, cable connectors, plugs, communication ports, electrical sockets, a card reader, a barcode reader, a biometric scanner, an interactive display screen, a printer, a temperature sensor, a light sensor, a disinfection level sensor, a proximity or distance or motion sensor, an accelerometer, a gyroscope, or any other types of sensors commensurate with the predefined or dynamically defined functions of the disinfector 100, etc.); or both. The interface(s) may facilitate communication between various devices or components operationally connected with the disinfector 100. In some embodiments, the interface(s) may facilitate communication with computing devices such as those mentioned above capable of interacting with the disinfector 100 over the network.

The disinfector 100 may be implemented as a standalone and dedicated device including hardware and installed software, where the hardware is closely matched to the requirements and/or functionality of the software. In some embodiments, the disinfector 100 may enhance or increase the functionality and/or capacity of the network to which it may be connected. Some embodiments may include the disinfector 100 including software, firmware, or other resources that support remote administration, operation, and/or maintenance of the disinfector 100. In some other embodiments, the disinfector 100 may operate, or not operate, in response to aspects or motions of wearable items and/or portable items, via a sensor, present within a predefined proximity of the disinfector 100. Examples of such items may include, but are not limited to, a fashion accessory (e.g., wristband, ring, watch, etc.), a utility device (e.g., stylus, pen, umbrella, watch, access control card, mobile phone, etc.), personal protective gear (e.g., gloves, masks, goggles, spectacles, helmets, clothing, etc.) or any combination thereof.

In some embodiments, the disinfector 100 either independently or in communication with a networked device may have video, voice, or data communication capabilities by being operationally coupled to, or including, various imaging devices (e.g., cameras, printers, scanners, etc.), various audio devices (e.g., microphones, music players, recorders, audio input devices, speakers, audio output devices, telephones, speaker phones, etc.), various video devices (e.g., monitors, projectors, displays, televisions, video output devices, video input devices, camcorders, etc.), or any other types of hardware, in any combination thereof. Other embodiments may additionally include the disinfector 100 being configured with one or more real time protocols (e.g., session initiation protocol (SIP), H.261, H.263, H.264, H.323, etc.) and non-real-time protocols known in the art, related art, or developed later to facilitate data transfer to the networked device, e.g., a computing device such as those discussed above.

As illustrated in FIG. 1, in one example, the disinfector 100 may have a substantially cuboidal shape; however, any other suitable shapes can be contemplated for the disinfector 100. The disinfector 100 may have a mobile body 102 including an assembly of parts configured to support, operate, and/or navigate the disinfector 100 or any components thereof. The mobile body 102 may include at least one mobility device operating to spatially move the disinfector 100 along a path and/or over a surface. The mobility device may be motorized or non-motorized. The mobility device may be automated or configurable for manual operation. In one example, as illustrated in FIGS. 1-6, the mobility device may include, but not limited to, a set of wheels, for example, wheels 104-1, 104-2, 104-3, and 104-4, hereinafter collectively referred to as wheels 104. Any suitable types of wheels known in the art including, but not limited to, omnidirectional wheels, mecanum wheels, and caster wheels may be employed that may allow the disinfector 100 to move (sideways, forward, rotate, backward, etc.) and to be relocated with precision to any desired target position or orientation in a room. Other examples may include the mobility device being adapted as an autonomous vehicle (not shown) to spatially drive the disinfector 100. The autonomous vehicle and/or motorized wheels such as the wheels 104 may be controlled by a control system, discussed below in detail, of the disinfector 100 or a remote computing device over the network.

In one embodiment, as illustrated in FIG. 1, the mobile body 102 may include a top panel 106-1, a front panel 106-2, a left panel 106-3, a right panel 106-4, and a rear panel 106-5 (collectively referred to as panels 106) substantially aligned with respective top, front, left, right, and rear surfaces of the disinfector 100. The panels 106 may define a cabinet 108 of the disinfector 100. The cabinet 108 may enclose a disinfection container 702 (shown in FIGS. 7-9) configured to receive and disinfect an article using electromagnetic radiation, discussed below in greater detail. The cabinet 108 may provide a housing, for example, formed by the panels 106 configured to restrict the UV light to pass therethrough, thereby preventing the UV light projected from the disinfection container 702 to exterior of the disinfector 100. In some instances, inner portions of the cabinet 108 may assist to limit the UV light up to an intended vertical or horizontal plane or surface within the disinfector 100. The cabinet 108 may additionally improve the aesthetics of the disinfector 100. The cabinet 108 may surround one or more components of the disinfector 100.

In the illustrated embodiment, the left panel 106-3 and the right panel 106-4 may include a first vent 110-1 and a second vent 110-2, hereinafter collectively referred to as vents 110, for allowing warm air around the operational components to dissipate into the ambient environment. Alternatively, the vents 110 may allow for air intake to cool the operational components within the cabinet 108. It would be appreciated that openings operationally similar to the vents 110 may be formed on any of the remaining panels 106 without allowing the UV light to escape from the cabinet 108 or the disinfector 100. The front panel 106-2 may extend along a front portion of the disinfector 100. In an embodiment, the front panel 106-2 may extend to cover such front portion and may be located under a front opening 112 of the disinfector 100. The front opening 112 may be horizontally aligned with the disinfection container 702, or any components thereof such as a tray 720 (shown in FIG. 7), inside the cabinet 108, discussed below in greater detail. Further, the top panel 106-1 may include a first portion 114-1 and a second portion 114-2 (hereinafter collectively referred to as sub-portions 114). The first portion 114-1 may substantially define a top portion of the disinfector 100. The first portion 114-1 may include outer edges extending into planes comprising the rear panel 106-5, the front panel 106-2, the left panel 106-3, and the right panel 106-4 to cover the top portion of the disinfector 100. The first portion 114-1 may include a front edge removably connecting to the second portion 114-2 arranged at a predefined angle relative to the first portion 114-1. For instance, the second portion 114-2 may be substantially perpendicular to the first portion 114-1. The second portion 114-2 may at least partially cover the front portion of the disinfector 100. In an embodiment, the second portion 114-2 of the cabinet 108 may include a cut-out defining the front opening 112 of the disinfector 100.

The cabinet 108 may also include components or pockets that may be permanently coupled, detachably connected, or integrally formed thereto based on intended purposes. For example, as illustrated in FIG. 1, the cabinet 108 may include a display unit 116 arranged on an outer surface of the cabinet 108 along the top portion of the disinfector 100. For example, the display unit 116 may be attached atop the top panel 106-1 or within an opening thereof. The display unit 116 may independently or in communication with a user interface (not shown) may indicate information pertaining to an operation of the disinfector 100. In one example, the display unit 116 may represent or include an interactive display screen allowing an operator to access, control, or dynamically define different functions of the disinfector 100. The display unit 116 may display a dashboard providing a list of functions, modes, parameters, avatars, etc. that the operator may select or modify for a desired operation of the disinfector 100. Other examples may include the display unit 116 including or operating in communication with a variety of tangible indicators (e.g., light emitting diodes, vibrators, speakers, etc.) or virtual indicators displayable on the dashboard, or any components operationally coupled to the display unit 116, to indicate different operational aspects of the disinfector 100. Examples of such virtual indicators may include, but are not limited to, numeric indicators, alphanumeric indicators, or non-alphanumeric indicators, such as different colors, different color luminance, different patterns, different textures, and different graphical objects. Examples of these operational aspects may include, but are not limited to, (i) values of operational parameters such as frequency, wavelength, duration, energy, and dose, (ii) different modes of operation and/or a selected mode in operation, (iii) operational states of different components, (iv) statuses of various operational tasks such as a disinfection cycle, network data transfer, and remote administration, (v) a number of disinfection cycles completed or run on the disinfector 100, and (vi) a number of flashes or pulses of a germicide (e.g., UV light) projected by the corresponding germicidal source or the disinfector 100.

The cabinet 108 may be made up of any durable, fire-retardant or fire-resistant, and light-weight materials known in the art, related art, or developed later including, but not limited to, metals, polymers, and/or alloys. Such materials may be substantially opaque to block the UV light; however, in some embodiments, the cabinet 108 may include portions including any suitable partially transparent material operating as an optical filter to restrict a germicidal light, such as the UV light, to pass therethrough. The cabinet 108 may cover, surround, or enclose one or more operational components of the mobile body 102.

Figure 2:
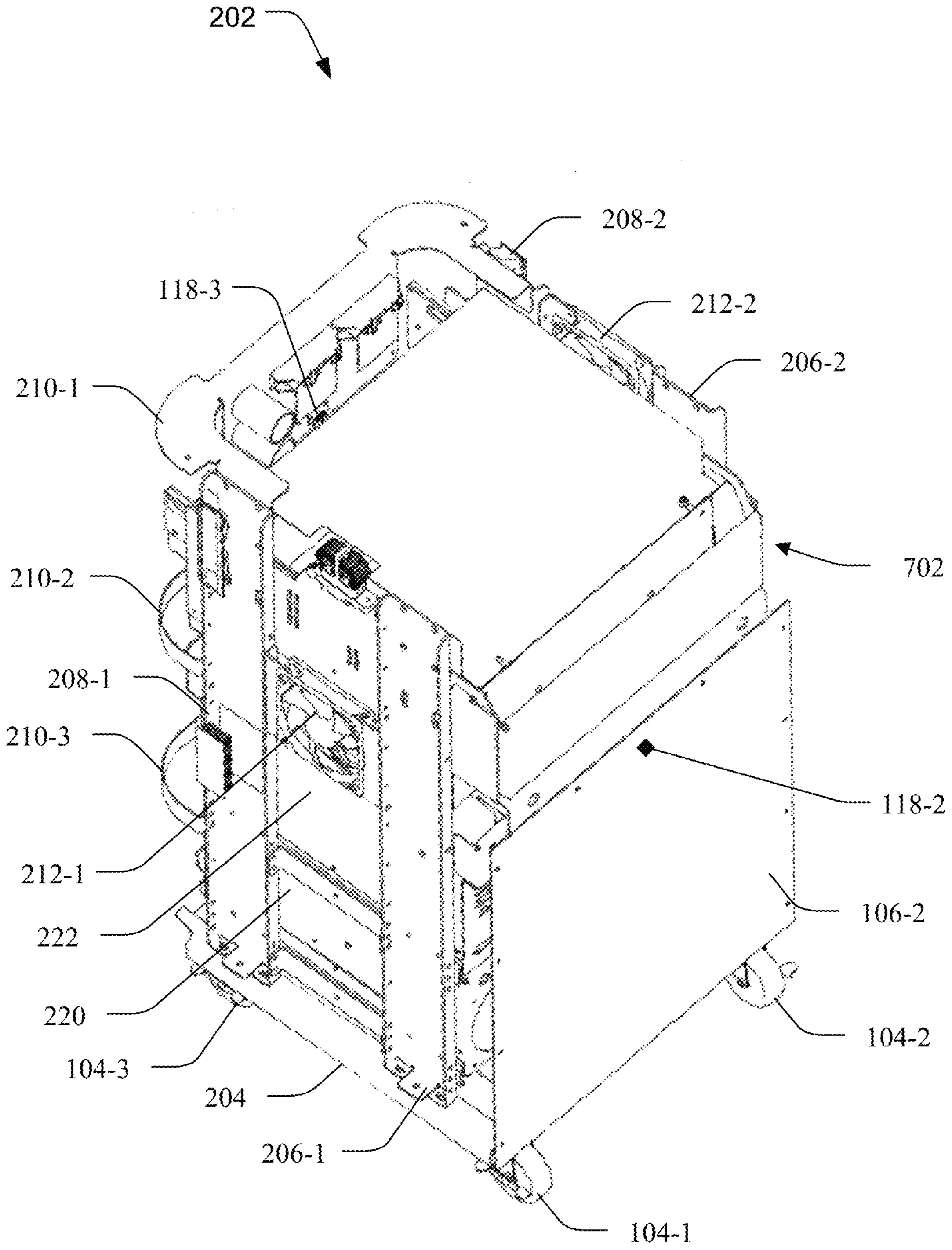
FIG. 2 is a front isometric view of a chassis for the UV disinfector of FIG. 1, according to a first embodiment of the present disclosure.

Further, the mobile body 102 may include a mobile frame to mount or support various components, such as the cabinet 108 and the disinfection container 702, of the disinfector 100. The mobile frame may have any suitable configuration including, but not limited to, shape, size, connectors, and/or openings depending on the components to be mounted or supported thereon. For example, in a first embodiment, as illustrated in FIG. 2, the mobile body 102 may include a "horizontal" chassis 202 defined by an assembly of parts mounted on a separate mobile carriage 204 having the wheels such as wheels 104. The chassis 202 may include a first vertical column 206-1 and a second vertical column 206-2 (collectively, referred to as front columns 206) arranged towards a front of the disinfector 100 and may be located proximate to a left edge and a right edge of the mobile carriage 204 respectively. The chassis 202 may also include a third vertical column 208-1 and a fourth vertical column 208-2 arranged towards a rear of the disinfector 100. Similar to the front columns 206, the third vertical column 208-1 and the fourth vertical column 208-2 (collectively, referred to as rear columns 208) may be located proximate to the left edge and the right edge of the mobile carriage 204 respectively.

The chassis 202 may also include a first separator 210-1, a second separator 210-2, and a third separator 210-3 (collectively, referred to as rear separators 210 210) connected to the rear columns 208. The rear separators 210 may extend outwardly between the rear columns 208. The rear separators 210 may assist to support the cabinet 108 and maintain a clearance space between the cabinet 108 and the components supported on the chassis 202 or the mobile carriage 204. The front columns 206 and the rear columns 208 may include slots or platforms (not shown) for defining horizontal compartments therebetween, thereby allowing the operational components such as a power supply 220 and a controller 222 (hereinafter collectively referred to as a control system) to be stacked one above the other. Further, the chassis 202 may include any suitable cooling system known in the art mounted thereto for dissipating heat accumulated around various components and/or portions of the disinfector 100. In one example, as illustrated in FIG. 2, the chassis 202 may include a first fan 212-1 and a second fan 212-2 (collectively, referred to as fans 212) removably attached thereto. Additionally, or alternatively, the chassis 202 may also include a vacuum source (not shown) to augment cooling by creating a negative air pressure within the cabinet 108 to draw out the warm air around various components, e.g., the disinfection container 702, supported by the chassis 202.

Figure 3:
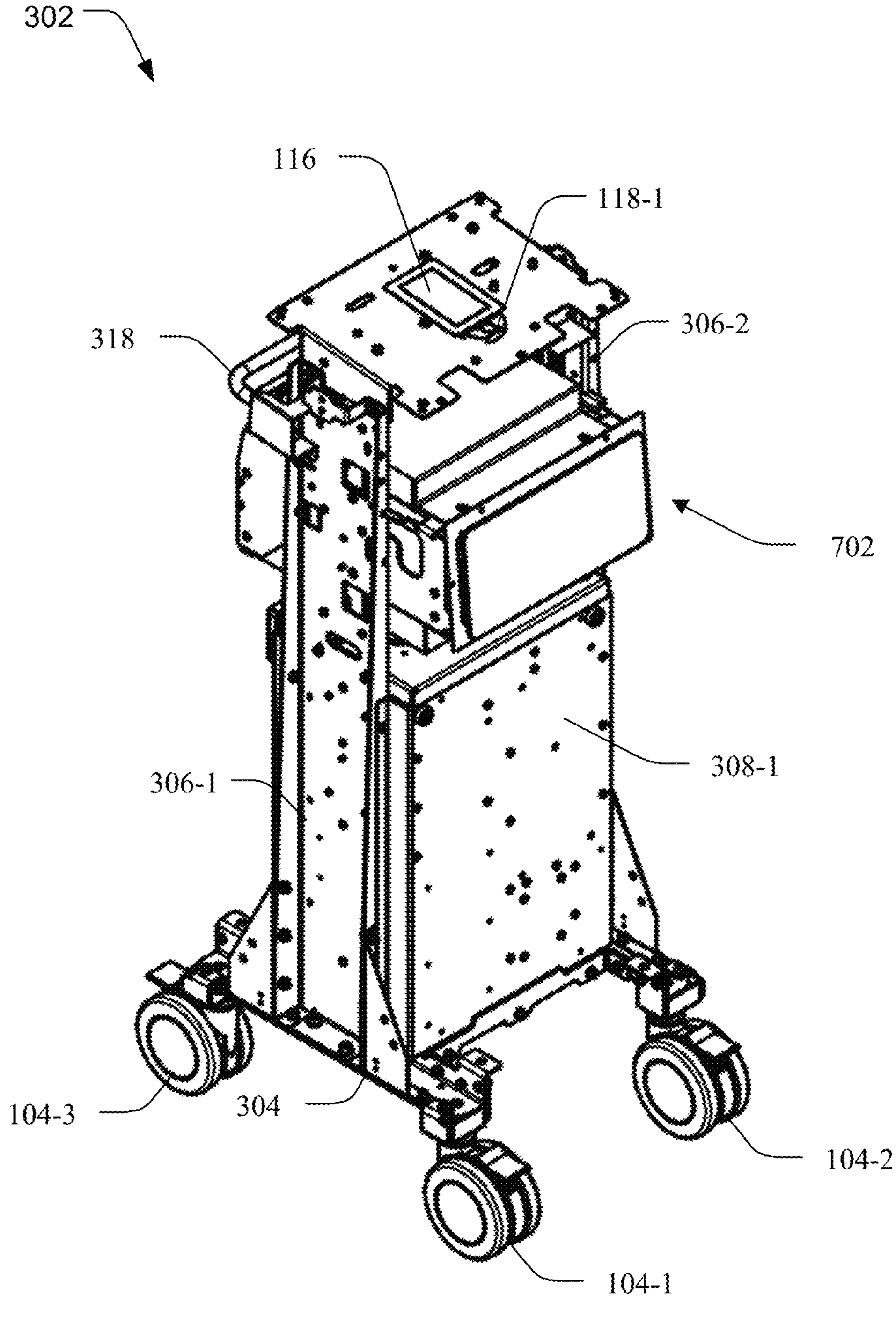
FIG. 3 is a front isometric view of an exemplary uniframe for the UV disinfector of FIG. 1, according to a second embodiment of the present disclosure.
Figure 4:
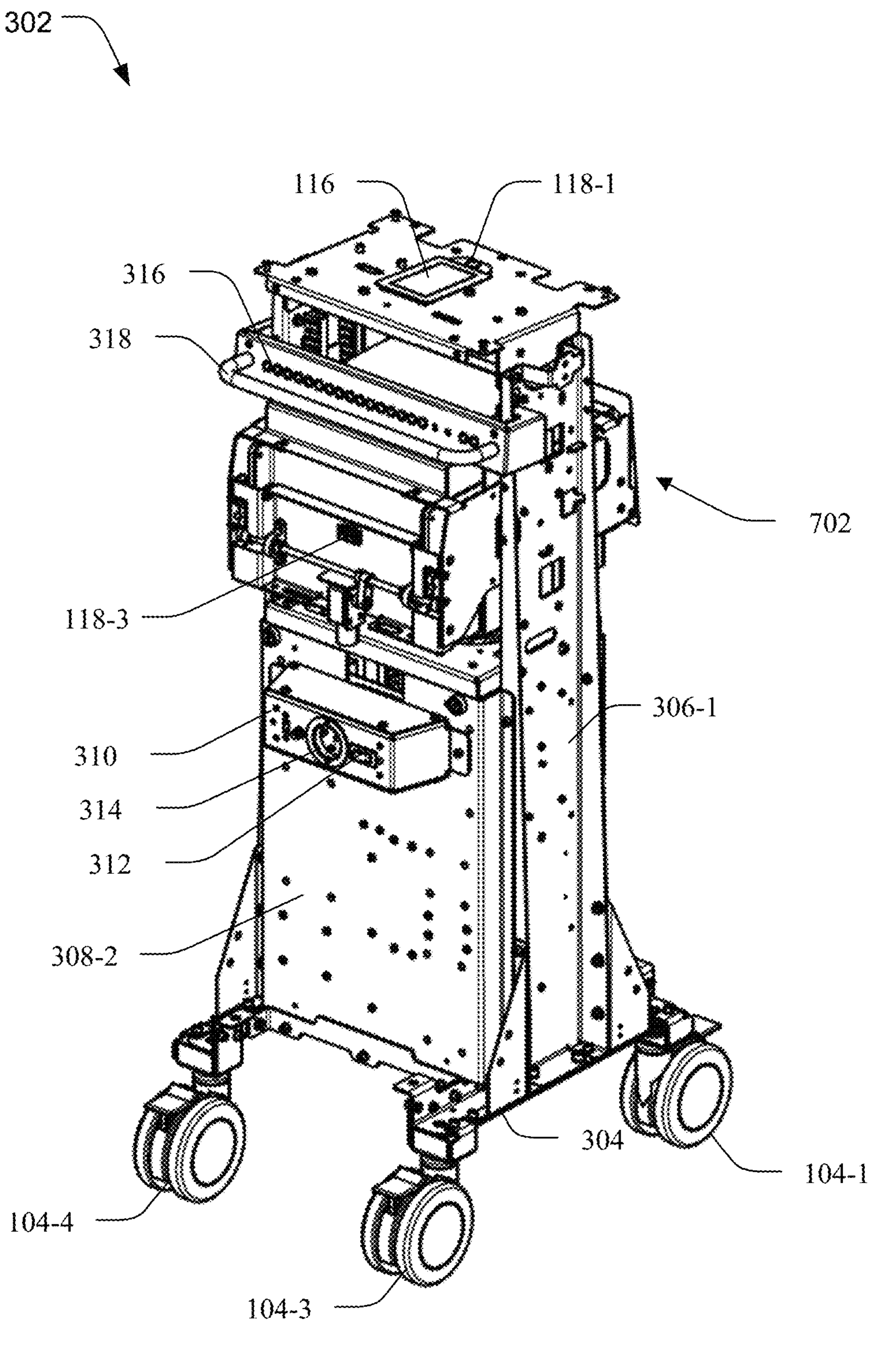
FIG. 4 is a rear isometric view of the uniframe of FIG. 3, according to the second embodiment of the present disclosure.

In a second embodiment, as illustrated in FIGS. 3-4, the mobile body 102 may include a uniframe 302 for the disinfector 100. The uniframe 302 may serve as an integral mobile frame to mount or support various operational components of the disinfector 100. As shown, the uniframe 302 includes a base 304 attached to wheels such as wheels 104, a vertical tray assembly, and a first column 306-1 and a second column 306-2 (hereinafter collectively referred to as columns 306). The vertical tray assembly may include a first tray 308-1 and a second tray 308-2 (hereinafter collectively referred to as vertical trays 308) and a hinge assembly (not shown). The vertical trays 308 may be disposed between the columns 306. The first tray 308-1 and the second tray 308-2 may be disposed towards front and rear portions of the uniframe 302, and that of the disinfector 100, respectively. The vertical trays 308 may have a similar geometry and/or dimensions for ease of construction and stability of the uniframe 302. Each of the vertical trays 308 may include an interior tray surface (not shown) providing a space to mount or support various operational components of the disinfector 100. For instance, the first tray 308-1 may carry low voltage components (e.g., controller 222) and the second tray 308-2 may carry high voltage components (e.g., power supply 220), or vice versa in other examples, on the respective interior tray surfaces.

Further, the vertical trays 308 may be pivotably attached to the uniframe 302 via any suitable hinge assembly known in the art for transitioning the vertical trays 308 between a closed position and an open position. In the closed position, as shown in FIGS. 3-4, the vertical trays 308 may be arranged parallel to a vertical axis of the uniframe 302 or the disinfector 100 such that the respective interior tray surfaces of the vertical trays 308 may be perpendicular to the base 304 of the uniframe 302 and oriented towards each other. Such vertical trays 308 may have a predefined separation therebetween in the closed position. Hence, unlike the "horizontal" chassis 202 providing for horizontal stacking of operational components one above the other, such vertical arrangement of operational components with the vertical trays 308 in the closed position enables an unobstructed airflow through the interior portion of the uniframe 302 for efficient cooling of the operational components during operation.

The vertical trays 308 may pivot to at least partially extend out from one of the front or rear sides of the uniframe 302 or the mobile body 102, to open up for replacement or maintenance of the components. In the open position (not shown), the vertical trays 308 may extend up to a predefined maximum pivot angle, for example, 45 degrees relative to a vertical axis of the uniframe 302 or the mobile body 102. However, other examples may include the maximum pivot angle being increased (e.g., up to approximately 90 degrees) or decreased (e.g., up to approximately 35 degrees).

Figure 6:
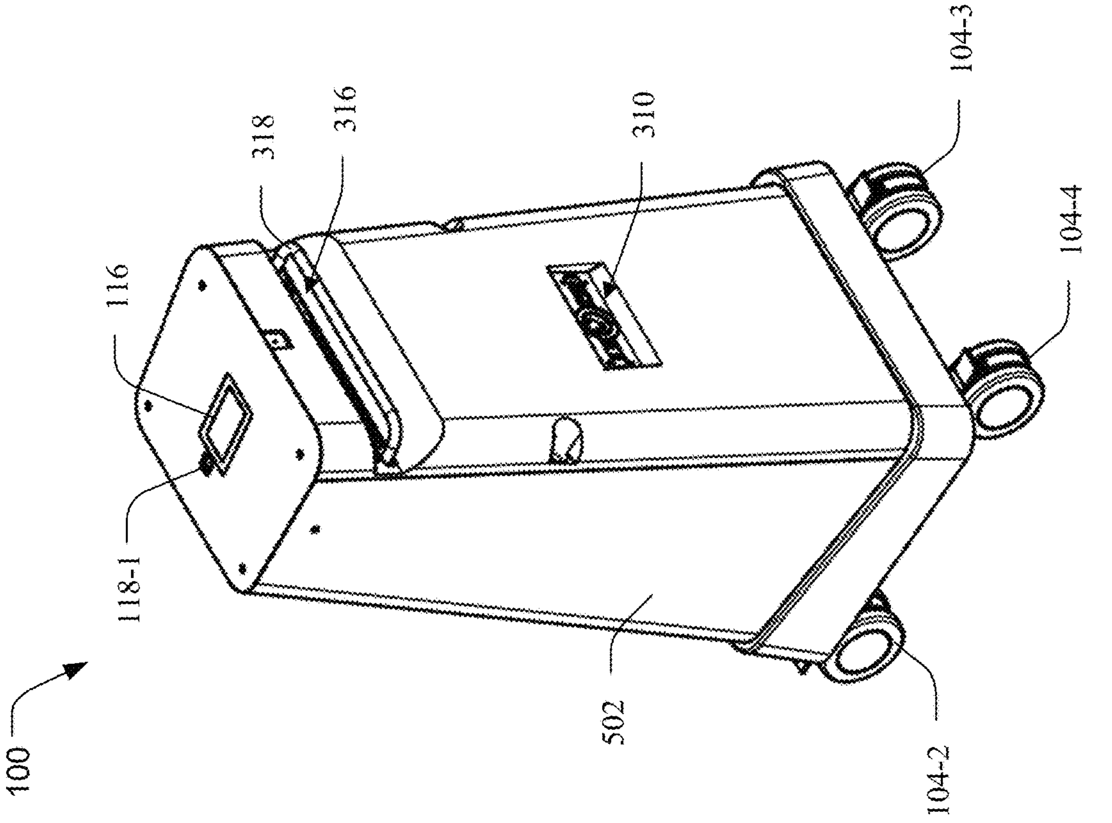
FIG. 6 is a rear isometric view of the UV disinfector of FIG. 5, according to an embodiment of the present disclosure.

The uniframe 302 may further include an auxiliary frame 310 towards a rear of the uniframe 302 and the mobile body 102. As illustrated in FIG. 4 and FIG. 6, the auxiliary frame 310 may be attached to the second tray 308-2 in the rear of the uniframe 302. The auxiliary frame 310 may be aligned horizontally (or vertically in some examples) and extend outwardly from the uniframe 302. The auxiliary frame 310 may have a fixed geometry; however, some examples may include the auxiliary frame 310 having portions made to selectively collapse or expand relative to the uniframe 302. The auxiliary frame 310 may include a socket 312 and a communication port 314 of any suitable types known in the art that may be coupled to the control system. The socket 312 may assist to connect a power cable for powering the disinfector 100 or a peripheral device (not shown). The communication port 314 (e.g., a Universal Serial Bus port) may assist with data transfer, e.g., to update firmware on the disinfector 100 or retrieve operational data stored in a computer memory of the disinfector 100.

Similar to the chassis 202, the uniframe 302 may also include any suitable cooling system known in the art mounted thereto for dissipating heat accumulated around various components and/or portions of the disinfector 100. In one example, the uniframe 302 may include a heat sink (not shown) and a cooling fan (not shown). In one instance, the heat sink (e.g., an active heat sink including a fan or a passive heat sink, or a combination thereof) may be embedded into an opening in the base 304. The cooling fan may be attached to the columns proximate to the disinfection container 702. For example, the cooling fan may create a positive airstream into the disinfection container 702 and the heat sink may create a negative airstream moving away from the uniframe 302 for a substantially downward airflow to remove heat from the disinfection container 702 and the operational components within the vertical trays 308 during operation. The uniframe 302 may further include a grid of holes or openings 316 (or simply opening grid 316) and a drive handle 318. The opening grid 316 may be located on a rear side of the uniframe 302 and proximate to the drive handle 318 and the disinfection container 702. The opening grid 316 may enable easy airflow for cooling the operation components within the uniframe 302. On the other hand, the drive handle 318 may also be located on the rear side of the uniframe 302 and in an upper section of the uniframe 302 or the mobile body 102. The drive handle 318 may assist a user to manually maneuver the disinfector 100 or the mobile body 102 from one position, or orientation, to another.

Figure 5:
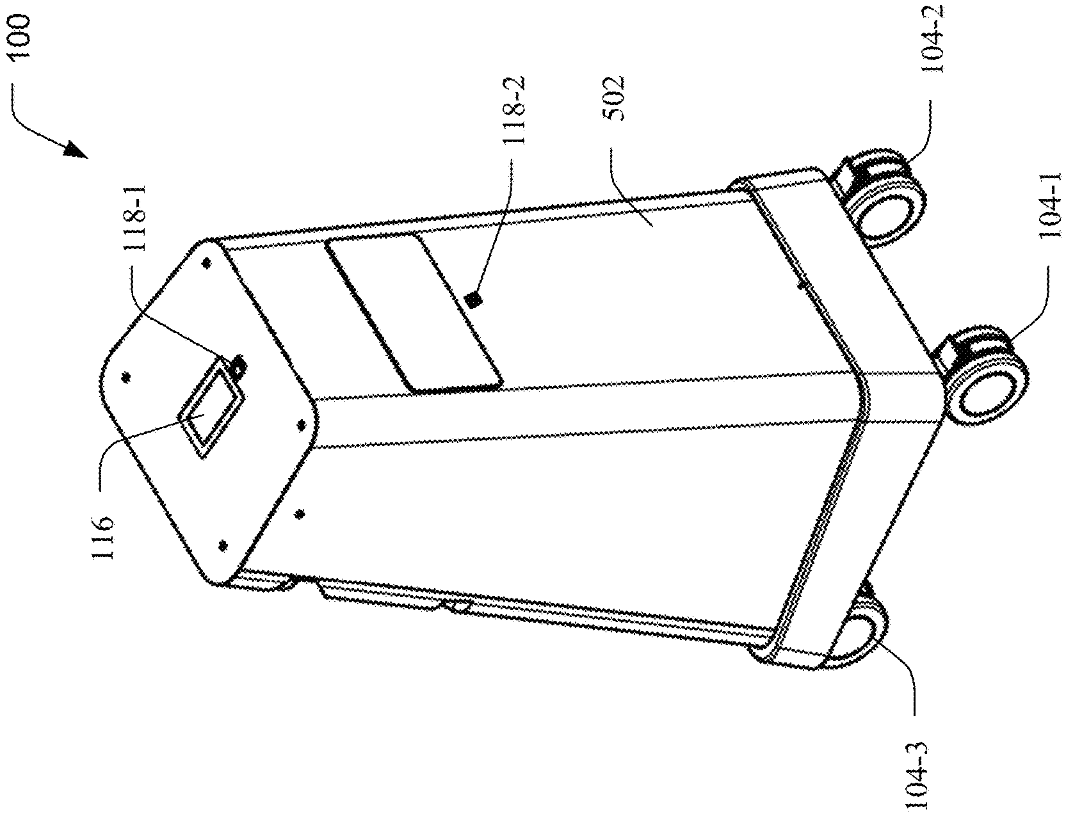
FIG. 5 is a front isometric view of an exemplary UV disinfector including the uniframe of FIG. 3, according to an embodiment of the present disclosure.

Further, the uniframe 302 may be covered by a casing 502, similar to the cabinet 108 as described above. The casing 502 may protect one or more components of the disinfector 100 from dust and damage. Such casing 502 may also assist to improve aesthetics of the disinfector 100. In one example, as shown in FIG. 5-6, the mobile body 102 may include the casing 502 formed out of a single panel or a set of panels to surround one or more components (e.g., the tray 720 assembly, the controller 222, a portion of the auxiliary frame 310, etc.) in the of the uniframe 302. As illustrated, the casing 502 may include various openings in the rear side of the uniframe 302 to respectively expose the auxiliary frame 310, the opening grid 316, the drive handle 318, the display unit 116, and the disinfection container 702. The casing 502 may have any suitable geometry and dimensions commensurate with a construction of the uniframe 302 for providing a desired shape, e.g., substantially a frustum shape as illustrated, to the disinfector 100. One having ordinary skill in the art would understand that the chassis 202 and the uniframe 302 may include additional elements including, without limitation, central pole or tower, compartments, partitions, protrusions, openings, and panels 106, to accommodate or support any further components or functionalities associated with the disinfector 100.

In one embodiment, the mobile body 102 further includes the disinfection container 702 mounted to the mobile frame, such as the chassis 202 and the uniframe 302, and located within the cabinet 108 and the casing 502 respectively. For the sake of simplicity and brevity, functionalities of the disinfection container 702 and the disinfector 100 will be discussed hereinafter with respect to the cabinet 108; however, one having ordinary skill in the art will understand that similar aspects of the cabinet 108 can be incorporated in the casing 502 for an intended operation of the disinfector 100 described in the present disclosure.

Figure 7:
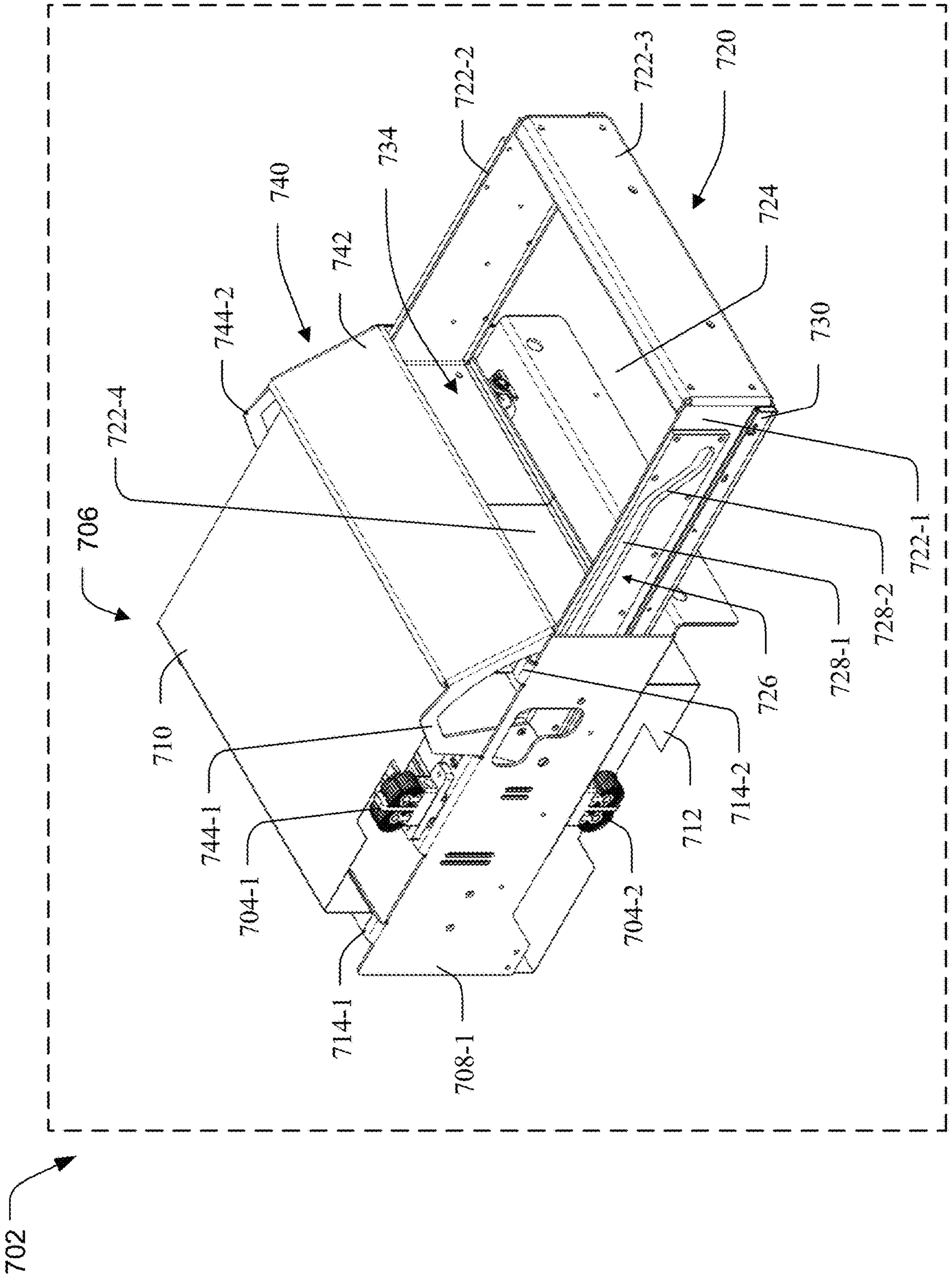
FIG. 7 is a front isometric view of an exemplary disinfection container for the UV disinfector of FIG. 1 and FIG. 5, according to an embodiment of the present disclosure.
Figure 8:
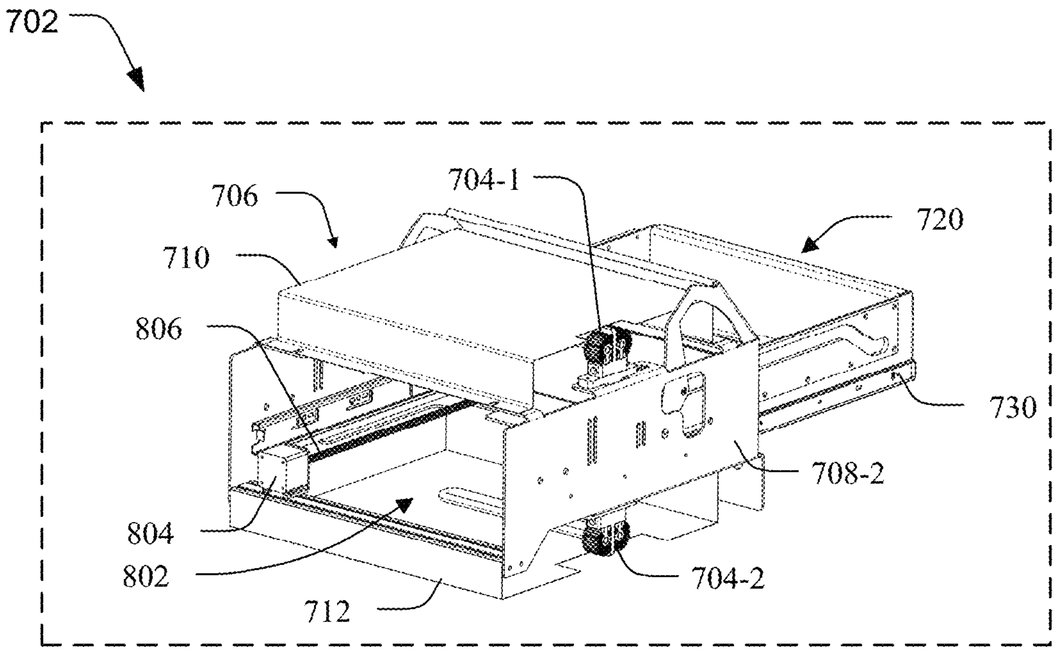
FIG. 8 is a rear isometric view of the disinfection container of FIG. 7, according to an embodiment of the present disclosure.
Figure 9:
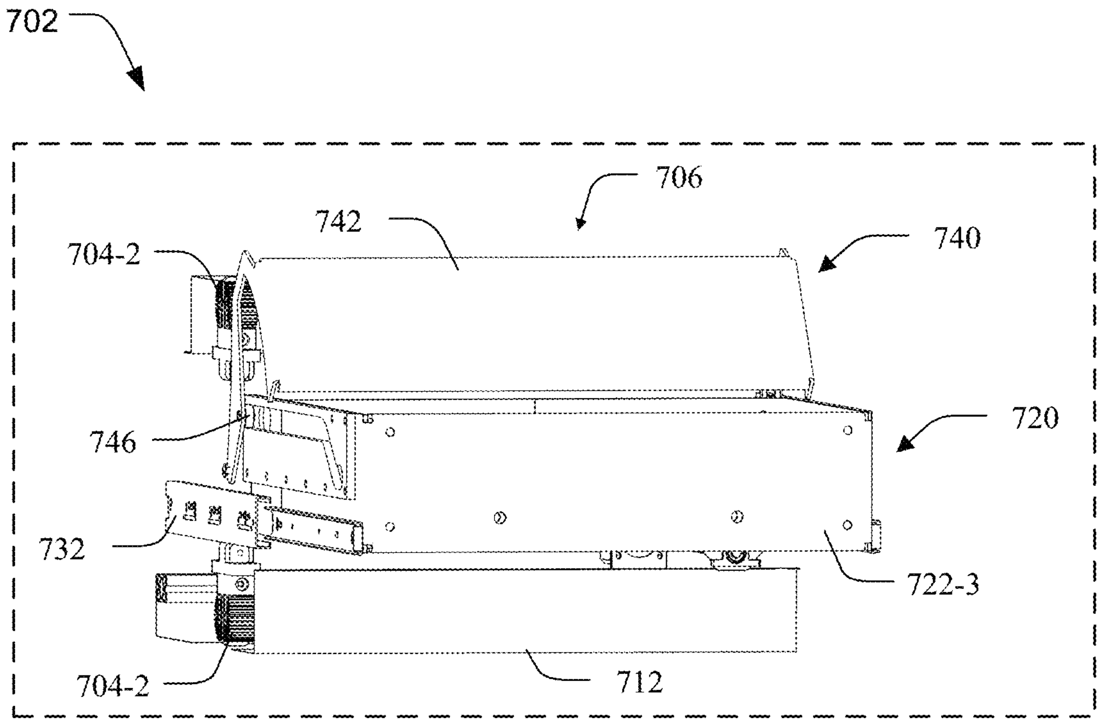
FIG. 9 is a front perspective view of the disinfection container of FIG. 7, according to an embodiment of the present disclosure.

The disinfection container 702 may be made distinct from the cabinet 108. The disinfection container 702 may be located in an upper section of the disinfector 100 and may be removably coupled to the mobile frame, such as the chassis 202 and the uniframe 302, using any suitable connection mechanism known in the art. Such removability of the disinfection container 702 from the mobile frame or the cabinet 108 may provide for easy maintenance and replacement thereof or those of any parts connected thereto. The disinfection container 702 may be implemented as a combination of movable portions and stationary portions. As illustrated in FIGS. 7-9, the stationary portions may include one or more germicide sources emitting any of the desired germicide noted above. In one example, the stationary portions may include a first radiation unit 704-1 and a second radiation unit 704-2 (collectively, referred to as radiation units 704) to emit germicidal radiation of any suitable wavelength capable of disinfecting a surface such as that of an article. In one embodiment, each of the radiation units 704 may operate as UV sources emitting UV light of a predetermined energy within a predetermined germicidal wavelength range including-280 nm (i.e., UV type C); 280-315 nm (i.e., UV type B); 200-300 nm (i.e., middle UV); and 122-200 nm (i.e., far UV). Other wavelength ranges may also be employed, including those providing ionizing radiation (e.g., extreme UV, with a wavelength of 10-120 nm). Each of the UV sources may be a pulsed radiation source, a continuous radiation source, or a set of both the pulsed radiation source and the continuous radiation source. The pulsed radiation source may be configured by the controller 222 to emit pulses of UV light of a predetermined energy intensity within a predefined or dynamically defined wavelength range. In some embodiments, the pulsed radiation source may be configured by the controller 222 to have a pulse frequency and/or pulse duration that may cause the emitted pulsed UV light to appear as continuous to a human eye. On the other hand, the continuous radiation source may be configured by the controller 222 to emit a continuous stream of UV light. In some embodiments, the continuous radiation source may be turned on and off at a predetermined frequency by the controller 222 to emit pulses of UV radiation. In one example, the UV source may be a strip of one or more UV light emitting diodes (LEDs) configured to emit pulses of UV light. Other examples may include UV lamps or bulbs configured for pulsed or near continuous emission of the UV light. In another embodiment, the radiation units 704 may additionally include other types of radiation sources and/or non-radiation sources capable of providing assistive agents for disinfection. Examples of such assistive agents may include, but are not limited to, chemical agents (e.g., alcohols, oxidizing agents, naturally occurring or modified compounds, etc.), physical agents (e.g., heat, pressure, vibration, sound, radiation, plasma, electric current, etc.), and biological agents (e.g., organisms, plants or plant products, organic residues, assistive-pathogens, etc.).

The stationary portions may also include a support frame 706 having a first side plate 708-1, a second side plate 708-2 (collectively, referred to as side plates 708), a top plate 710, and a bottom plate 712. The side plates 708 may be located between the bottom plate 712 and the top plate 710. The bottom plate 712 may be connected to the side plates 708, which may be arranged in the same plane; however, in some embodiments, each of the side plates 708 may be located in a different plane. The bottom plate 712 may be arranged proximate to lower edges of the side plates 708. The bottom plate 712 may assist to keep a fixed separating distance between the side plates 708. The bottom plate 712 may be substantially located in a plane below the side plates 708. The bottom plate 712 and the side plates 708 may include gaps (or holes in some examples) therebetween for easy air circulation to dissipate heat therefrom. Further, the support frame 706 may include a first frame separator 714-1 and a second frame separator 714-2 (collectively, referred to as frame separators 714). Each of the frame separators 714 may be connected to the side plates 708. The frame separators 714 may be arranged proximate to upper edges of the side plates 708 and may extend outwardly therefrom. The frame separators 714 may be configured to connect with the top plate 710 and may be located substantially in a plane above the side plates 708. The top plate 710 may be removably attached to the frame separators 714. The top plate 710 may have an upper surface extending above the frame separators 714 to accommodate one of the radiation units 704, thereby creating gaps between the top plate 710 and the side plates 708. The gaps may allow for easy air circulation therethrough and assist in removing heat proximate to the radiation units 704. The inner surfaces of the bottom plate 712, the side plates 708, and the top plate 710 may be made reflective, where the inner surfaces may be proximate to the tray 720. For example, the side plates 708, the bottom plate 712, and the top plate 710 may be fabricated from a metal such as aluminum, such that respective inner surfaces, orientated towards the radiation units 704, may be polished to operate as reflectors. Other examples may include such inner surfaces being treated or overlaid with materials (e.g., paint, plating, mirrors, lens, etc.) capable of redirecting or reflecting the UV light towards the tray 720. Further examples may include the disinfection container 702 including a camera (not shown) located inside the disinfection container 702 or the cabinet 108, and removably attached to an inner surface of the support frame 706 or the cabinet 108. The camera may operate in communication with the controller 222 to detect and/or recognize articles placed in the tray 720 upon being received at least in-part within the disinfection container 702.

The side plates 708 may provide supports, or openings, to mount the radiation units 704 thereon. As illustrated in FIGS. 7-9, the radiation units 704 may be removably attached to the side plates 708 using any of a variety of connection mechanisms known in the art. The radiation units 704 may be positioned opposite to each other. For example, the first radiation unit 704-1 and the second radiation unit 704-2 may be connected proximate to a top edge and a bottom edge of the first side plate 708-1 respectively. Accordingly, the radiation units 704 may be located or attached along the same vertical plane but different horizontal planes. In another example, each of the radiation units 704 may be attached on opposite side plates 708. Accordingly, the radiation units 704 may be substantially located or attached along the same horizontal plane but different vertical planes. Such arrangement of the first radiation unit 704-1 and the second radiation unit 704-2 may provide an open region therebetween within the support frame 706. The open region 802 (hereinafter referred to as moveable region 802) may be configured to accommodate the movable portions, or parts thereof, of the disinfector 100.

In one embodiment, the movable portions may include the tray 720 and a barrier 740. The tray 720 may be operable to move between an extended position outside the cabinet 108 for placement and retrieval of an article in the tray 720 and a retracted position within the disinfection container 702 for disinfecting the article. In the disinfection container 702, the tray 720 may be configured for being accommodated within the moveable region 802 between the radiation units 704. Hence, the first radiation unit 704-1 may be located between the top plate 710 and the tray 720. Similarly, the second radiation unit 704-2 may be located between the bottom plate 712 and the tray 720. In one example, the tray 720 may include a left side wall 722-1, a right side wall 722-2, a front wall 722-3, and a rear wall 722-4 (collectively referred to as tray walls 722). The tray walls 722 may provide a space between them defining a tray base with such space having dimensions commensurate with those of the moveable region 802. The tray 720 includes the tray base 724 for receiving one or more articles for disinfection. The tray base 724 may extend across, and surrounded by, the tray walls 722. The tray base 724 may be made up of any suitable material (e.g., quartz) that is permeable to the germicide such as the UV light. In some embodiments, the tray base 724 may, additionally or alternatively, include gaps or perforations (not shown) to allow further penetration of the germicide such as the UV light therethrough. In some other embodiments, the tray base 724 may include partitions (not shown) having reflective surfaces to create multiple chambers for receiving the articles. The inner surfaces of the tray walls 722 may be polished, and/or treated or overlaid with materials (e.g., paint, plating, mirrors, lens, etc.) capable of redirecting or reflecting the UV light substantially towards a plane containing the tray base 724.

Further, the tray 720 may be configured to move in a plane containing the moveable region 802 between the radiation units 704 using any suitable mechanism known in the art. For example, outer surfaces of both the left side wall 722-1 and the right side wall 722-2 may have tracks (or channels), such as a track 726 (FIGS. 7-8) along the left side wall 722-1. Each of the tracks may include an elongated portion 728-1 and an angled portion 728-2. The elongated portion 728-1 may be longer than the angled portion 728-2 and extend along a substantial length of the tray 720. The elongated portion 728-1 may be parallel to a length of the tray 720 and aligned with the side plates 708. Relative to the elongated portion 728-1, the angled portion 728-2 may be located proximate to the front wall 722-3 of the tray 720 and may slant downwards at a predefined angle towards a front of the tray 720. The tracks may be configured to communicate with a portion of the barrier 740, discussed below in further detail. Further, each of the left side wall 722-1 and the right side wall 722-2 may also include a slider 730, which may communicate with a guide 732 fitted on the corresponding inner surfaces of the side plates 708. The slider-guide arrangement may support the tray 720 and allow the tray 720 to slide thereon. It will be appreciated that the tray 720 may be made to move using any suitable sliding mechanism known in the art, related art, or developed later including a ball-screw mechanism. In an embodiment, the tray 720 may be controllably driven for being extended in and out of the support frame 706 or the disinfection container 702 and/or the cabinet 108 using any suitable driving mechanism known in the art, related art, or developed later. For example, as illustrated in FIG. 8, the tray 720 may be driven based on a leadscrew mechanism implemented using a motor 804, e.g., located proximate to the rear wall 722-4 of the tray 720. The motor 804 may operate as an actuator and be supported by the bottom plate 712 towards a rear end of the support frame 706 for driving a leadscrew such as a leadscrew 806 connected to the tray 720. Upon being driven, the leadscrew 806 may convert a rotary motion of the motor 804 to a linear motion of the tray 720. Any suitable type of motor 804 known in the art may be used including, but not limited to, a brushed motor, a brushless motor, a servo motor, and a stepper motor. Other embodiments may include any other suitable mechanisms for driving a linear motion of the tray 720. For example, the tray 720 may implement a belt-clamp arrangement (not shown) being operationally connected to the motor 804. The rotation of the motor 804 may rotate a belt for driving the tray 720 in and out of the disinfection container 702, where the clamp may operate as a brake controlled by the controller 222 for controlling a movement of the belt, and hence that of the tray 720. The tray 720 may extend in and out of the disinfection container 702 through an open end 734 of the support frame 706. The tray 720 may operate in tandem with the barrier 740.

In one embodiment, the barrier 740 may be configured to pivot about a horizontal axis. The barrier 740 may include a front cover 742, a first curved arm 744-1, and a second curved arm 744-2 (collectively referred to as curved arms 744). The curved arms 744 may be connected to lateral ends of the front cover 742. The front cover 742 may have a suitable geometry and dimensions to substantially cover a front region or the open end 734 of the support frame 706. The open end 734 may be aligned with the front opening 112 of the disinfector 100. In some embodiments, such front region or the open end 734 may extend between the bottom plate 712 and the top plate 710.

Further, the curved arms 744 may be rotatably or pivotally coupled to the tray 720 via cams, such as a cam 746, along the tracks. The cams moving along the tracks may assist to convert a linear motion of the tray 720 into a rotary motion of the curved arms 744 for pivoting the barrier 740 about the horizontal axis. The barrier 740 may pivot to transition between an open position and a closed position. In the open position, the cams may engage with the elongated portions, e.g., the elongated portion 728-1, of the tracks to move, e.g., rotate or pivot, the curved arms 744 for positioning the front cover 742 above or along the top plate 710, thereby keeping the barrier 740 away from the front opening 112 of the disinfector 100. However, in some embodiments, the curved arms 744 may be configured to rotate or pivot for positioning the front cover 742 below or along the bottom plate 712. Accordingly, the front cover 742 may be positioned away from a plane containing the tray 720, the moveable region 802, and the front opening 112 in the open position of the barrier 740. Hence, the barrier 740 may be moved upwards for being positioned away from a moving path of the tray 720 and the front opening 112 while the tray 720 may be extending out of the disinfection container 702. In the closed position, the cams may engage with the respective angled portion 728-2*s* of the tracks to pivot the curved arms 744 for aligning the front cover 742 with the plane containing the tray 720, the movable region, and/or the front opening 112 of the disinfector 100. Accordingly, the front cover 742 may be positioned in the plane containing the tray 720 or the moveable region 802 in the closed position. For example, the front cover 742 may be located opposite the front wall 722-3 of the tray 720 while the tray 720 may be positioned substantially within the support frame 706, thereby positioning the barrier 740 in the moving path of the tray 720 420. The front cover 742, and hence the barrier 740, may align with the front opening 112 of the disinfector 100 in the closed position. The positions of the tray 720, e.g., for driving the barrier 740, may be monitored using any of a variety of sensors.

Further, the disinfector 100 may include a top sensor 118-1, a front sensor 118-2, and a rear sensor 118-3, hereinafter collectively referred to as sensors 118, of any suitable type known in the art, related art, or developed later based on an intended operation and/or placement. Each of the sensors 118 may assist with start and stop operations of the disinfector 100, or various components thereof. For example, as illustrated in FIG. 1, the top sensor 118-1 (e.g., a proximity sensor such as an ultrasonic sensor, etc.) may be located on the top panel 106-1 of the protection cabinet 108; however, any other suitable location may be contemplated. The top sensor 118-1 may assist to control or maneuver a forward/outward or a backward/inward motion of the tray 720 for being extended in and out of the support frame 706 and/or the disinfector 100. On the other hand, as illustrated in FIG. 1 and FIG. 5, the front sensor 118-2 (e.g., a proximity sensor, etc.) may be located proximate to (i) the front opening 112, (ii) the cut-out of the second portion 114-2 of the top panel 106-1 or (iii) an outer surface of the front wall 722-3 of the tray 720. The front sensor 118-2 may assist to detect presence of an object in a forward/outward moving path of the tray 720 outside the disinfector 100. Further, as illustrated in FIG. 2 and FIG. 4, the rear sensor 118-3 (e.g., a proximity sensor such as an ultrasonic sensor and a mechanical switch, etc.) may be removably connected to the chassis 202 towards a rear end of the disinfection container 702 or the tray 720. The rear sensor 118-3 may monitor a position of the tray 720 and assist with start and stop operations of the motor 804 for driving the tray 720 up to an intended distance in forward/outward direction as well as a backward/inward direction. The operations of the sensors 118, the motor 804, the radiation units 704, and/or any automated movement of the disinfector 100, or any components thereof including the display unit 116, may be controlled or driven by the control system of the disinfector 100.

The control system may include the power supply 220 and the controller 222. The power supply 220 may be a high voltage power supply 220 delivered from an external electrical outlet via a power cord or from a set of one or more batteries placed on the mobile frame, such as the chassis 202 or the uniframe 302, of the disinfector 100. The controller 222 may be an electronic or an electromechanical device configured to control predefined or dynamically defined functions and movements of various components including, but not limited to, the mobile carriage 204, the display unit 116, disinfection container 702, and the motorized wheels such as wheels 104 operationally connected to the disinfector 100. In some embodiments, the controller 222 may include or be implemented by way of a single device (e.g., a computing device, processor or an electronic storage device) or a combination of multiple devices. The controller 222 may be implemented in hardware or a suitable combination of hardware and software. The “hardware” may comprise a combination of discrete electronic or electromechanical components, an integrated circuit, an application-specific integrated circuit, a field programmable gate array, a digital signal processor, or other suitable hardware. The “software” may comprise one or more objects, agents, threads, lines of code, subroutines, separate software applications, two or more lines of code or other suitable software structures operating in one or more software applications.

Operation

In one embodiment, the controller 222 may control various components and functions of the disinfector 100. During operation, the controller 222 may operate the disinfector 100 in a normal mode or an automated mode (hereinafter collectively referred to as device modes). In the automated mode, the controller 222 may (a) drive the mobility device, such as the autonomous vehicle or the motorized wheels such as the wheels 104, autonomously or via a remote device for moving or orienting the disinfector 100 to a target position or orientation, and/or (b) allow for remote controlling of the germicidal sources within the disinfector 100 for activating or inhibiting (or stop) projection of a germicide such as UV light. In the normal mode, the controller 222 may enable an operator to manually move or steer the mobility device, for example, autonomous vehicle or the motorized wheels such as the wheels 104. In another example, the controller 222 may additionally operate the disinfector 100 in one of a time mode and an object mode (hereinafter collectively referred to as disinfection modes). In the time mode, the controller 222 may activate the germicidal sources such as the radiation units 704 to emit UV light for a predefined duration (e.g., 30 seconds) defining a first disinfection cycle. In the object mode, the controller 222 may activate the germicidal sources such as the radiation units 704 to emit UV light for a predefined duration based on a type of article to be disinfected (e.g., 30 seconds for a non-permeable article such as an electronic device and 45 seconds for a permeable article such as a facial mask), thereby defining a second disinfection cycle.

Each of the device modes and the disinfection modes (collectively referred to as the operational modes) may be implementable to operate independently, or in tandem with each other, in any suitable combination or order. However, some examples may include a particular operational mode being operable mutually exclusive to one or more of the remaining operational modes. For instance, the controller 222 may implement the automated mode based on the disinfection modes and the normal mode being deactivated. In some instances, the controller 222 may automatically deactivate the automated mode based on any of the disinfection modes and the normal mode being selected. These operational modes may be selected by a user using any of the suitable input devices known in the art. For example, the user may login on an input device such as the display unit 116 and an interactive display screen of a mobile computing device operating in communication with the controller 222 of the disinfector 100 to select one or more of these modes for operation.

Figure 10B:
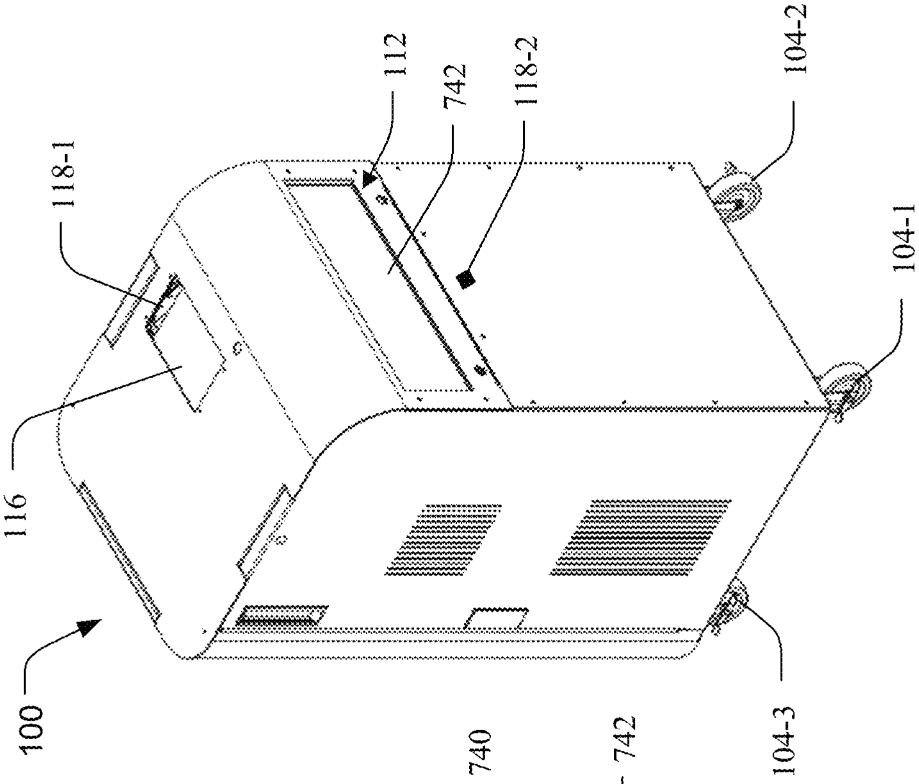
FIG. 10B is a front isometric view of the UV disinfector of FIG. 1 including the disinfection container of FIG. 10A, according to an embodiment of the present disclosure.
Figure 10A:
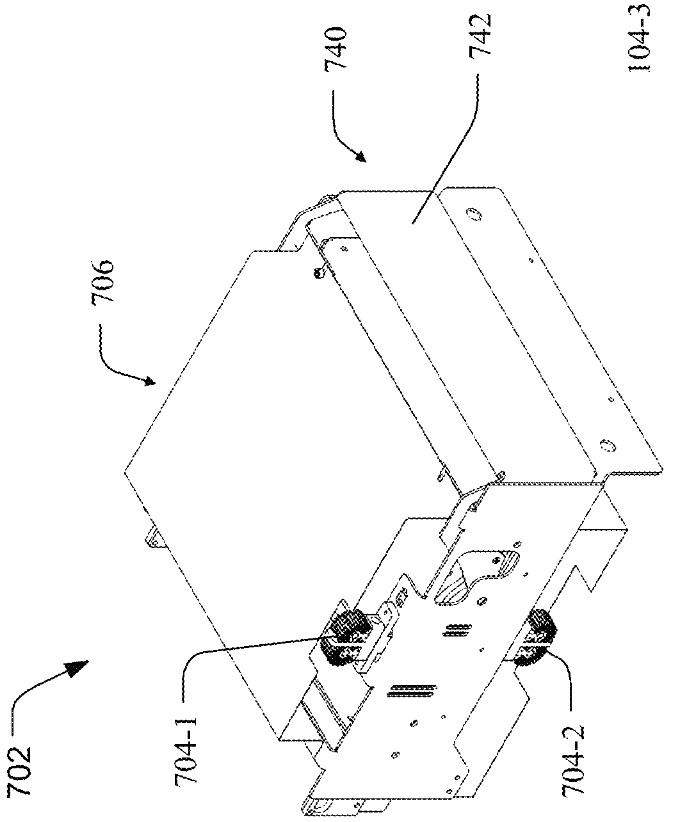
FIG. 10A is a front isometric view of the disinfection container of FIG. 7 including a closed barrier and a retracted/non-extended tray, according to an embodiment of the present disclosure.
Figure 10D:
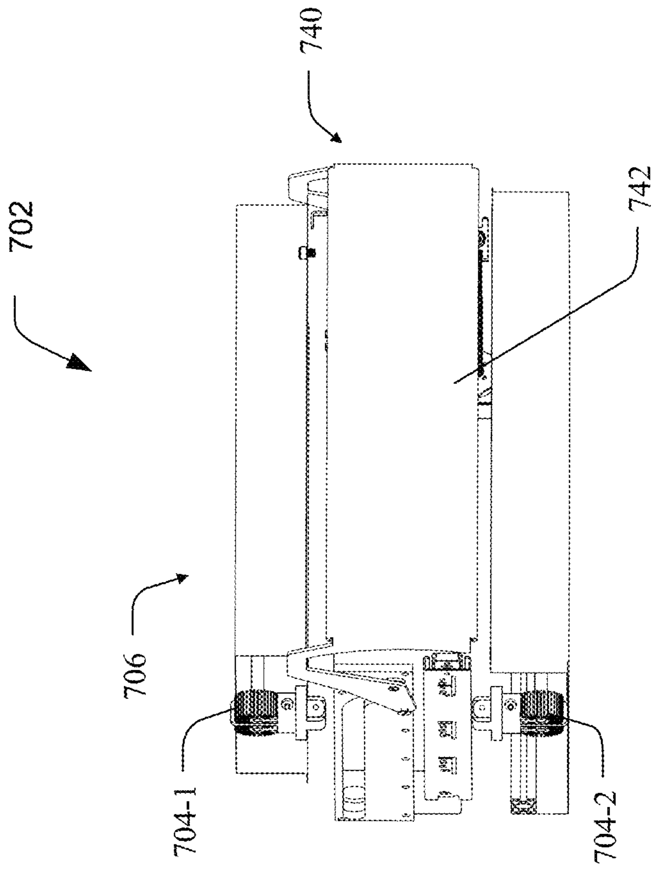
FIG. 10D is a front perspective view of the disinfection container of FIG. 10A, according to an embodiment of the present disclosure.
Figure 10C:
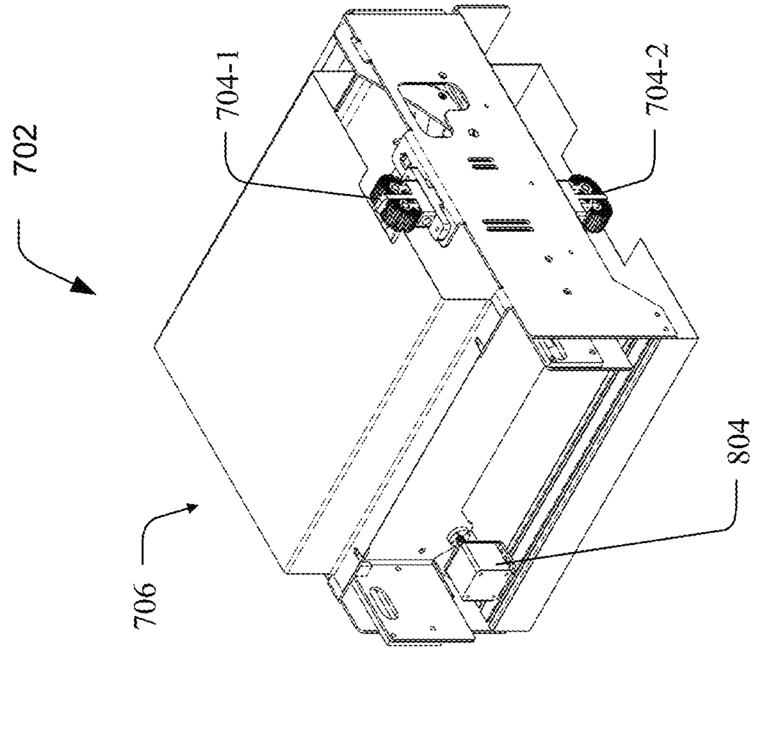
FIG. 10C is a rear isometric view of the disinfection container of FIG. 10A, according to an embodiment of the present disclosure.

As illustrated in FIG. 10A, when the disinfector 100 may be powered-on, the tray 720 may be set in a retracted or non-extended position within the disinfector 100. In the retracted position, the tray 720 may be substantially positioned within the disinfection container 702. Moreover, the barrier 740 may be set in the closed position with the front cover 742 aligned with the front wall 722-3 of the tray 720. In the closed position, as illustrated in FIG. 10B, the tray 720 as well as the barrier 740 may be located inside the cabinet 108 such that the barrier 740 may block the front opening 112 of the disinfector 100. The rear wall 722-4 of the tray 720 may be located proximate to the motor 804 (FIG. 10C) and the cams such as the cam 746 of the barrier 740 may be engaged with the angled portion 728-2 of the tracks such as the track 726 for keeping the front cover 742 of the barrier 740 in the moving path of the tray 720 420, outside the support frame 706 (FIG. 10D). Additionally, the sensors 118 and the display unit 116 may be activated by the controller 222 for controlling the tray 720 for being transitioned between the non-extended/retracted position and an extended position outside the cabinet 108. The tray 720 may be operable by the controller 222 to extend outside of the disinfector 100 through the front opening 112 in the extended position.

The controller 222 may be configured to drive the tray 720 via the motor 804 from the non-extended or retracted position to the extended position based on predefined or dynamically defined conditions. For example, the controller 222 may be configured to drive the tray 724 based on signals received from the sensors such as the top sensor 118-1 and the front sensor 118-2. Both the top sensor 118-1 and the front sensor 118-2 may be configured to provide signals indicating a value ‘1’ to the controller 222 upon detecting any obstruction or motion within predefined or dynamically defined distances (e.g., up to at least approximately 5 inches) therefrom and otherwise indicating a value ‘0’ to the controller 222. The sensor signals may be received as a signal set (X, Y) where X, or a first value, may refer to a value indicated by a first signal from the top sensor 118-1 and Y, or a second value, may refer to a value indicated by a second signal from the front sensor 118-2. For instance, in the absence of any such obstruction or motion, the controller 222 may receive the signal set (0,0) from the top sensor 118-1 and the front sensor 118-2 respectively. In one embodiment, the controller 222 may be configured to activate the motor 804 to drive the tray 720 via the leadscrew mechanism based on the first signal indicating a value '1' and the second signal indicating a value '0.' The value '1' from the top sensor 118-1 may be provided, e.g., based on a user waving his/her hand across the top sensor 118-1, thereby supporting a touchless operation of the disinfector 100. The value '0' from the front sensor 118-2 may indicate that a clear moving path up to a predefined minimum distance being available near the front panel 106-2 of the cabinet 108 for extending the tray 720 outside the disinfector 100 without any obstructions. In one example, the minimum distance may be at least one-fourth of a length of the tray 720; however, other examples may include the minimum distance ranging from 4 inches to 10 inches. Accordingly, the controller 222 may begin driving the tray 720 towards the extended position upon receiving the signal set (1, 0). In some embodiments, the controller 222 may also begin driving the tray 720 towards the extended position based on a received signal set being (0, 0).

Figure 11B:
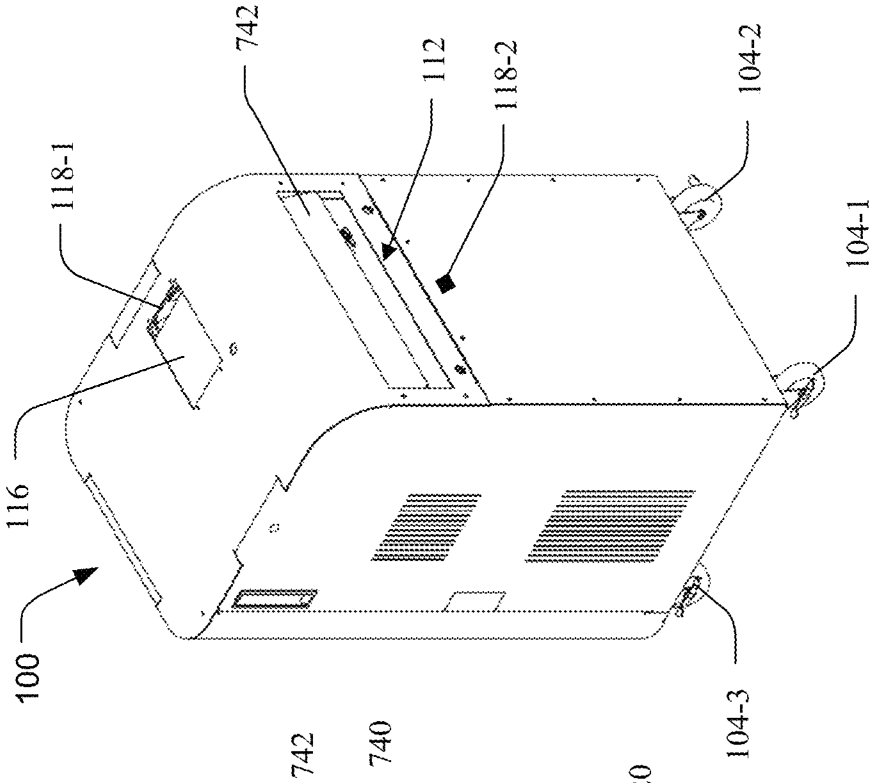
FIG. 11B is a front isometric view of the UV disinfector of FIG. 1 including the disinfection container of FIG. 11A, according to an embodiment of the present disclosure.
Figure 11A:
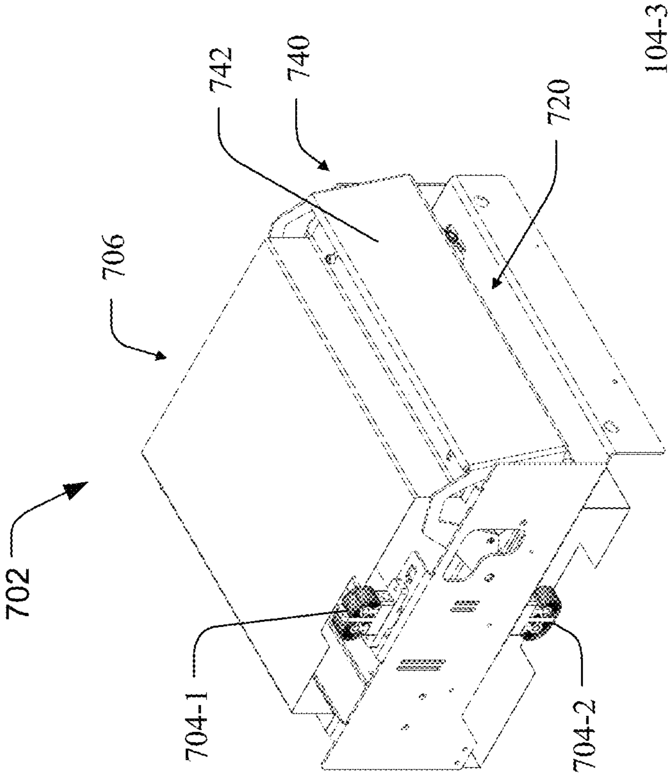
FIG. 11A is a front isometric view of the disinfection container of FIG. 7 including a partially-open barrier and a retracted/non-extended tray, according to an embodiment of the present disclosure.
Figure 11D:
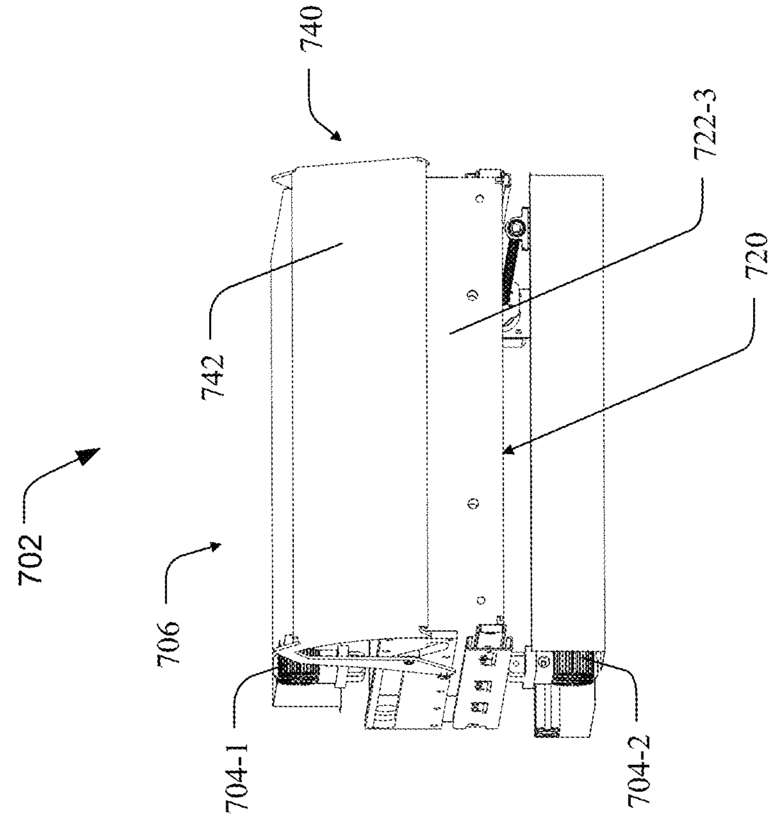
FIG. 11D is a front perspective view of the disinfection container of FIG. 11A, according to an embodiment of the present disclosure.
Figure 11C:
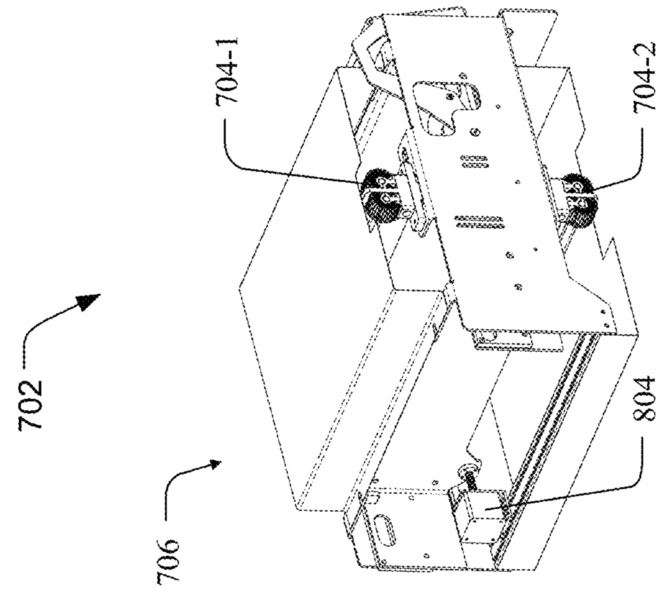
FIG. 11C is a rear isometric view of the disinfection container of FIG. 11A, according to an embodiment of the present disclosure.

The controller 222 may the trigger the motor 804 to drive a forward/outward motion of the tray 720 from the disinfection container 702 towards the extended position (FIG. 11C). Upon being driven (FIG. 11A), the tray 720 may begin to move out of the support frame 706 while beginning to move the front cover 742 of the barrier 740 away from the front wall 722-3 of the tray 720 and the front opening 112 of the disinfector 100. The front cover 742, and hence, the barrier 740, may begin to pivot upwards (FIG. 11A and FIG. 11D) to partially unblock the front opening 112 of the disinfector 100 (FIG. 11B). Such upward movement of the barrier 740 assists in avoiding any accidental pinching of fingers of a user from being caught between the barrier 740 and the front opening 112 of the disinfector 100. The upward movement be caused by the cams transitioning from the angled portion 728-2 to engage with the elongated portion 728-1 of the tracks for moving the front cover 742 of the barrier 740 partially away from the moving path of the tray 720 outside the support frame 706 (FIG. 11D). During movements of the tray 720, the rear sensor 118-3 may monitor positions of the tray 720 relative to the support frame 706 or the disinfection container 702. In some embodiments, the controller 222 may change the previously received value of the first signal from '1' to '0' after the controller 222 may have triggered the motor 804 for driving the tray 720 to the extended position. Such change in the received signal value from the top sensor 118-1 may assist to reuse the top sensor 118-1, e.g., based on a user waving his/her hand across the top sensor 118-1, for transitioning the tray 720 from the extended position back to the non-extended or retracted position, thereby further automating or supporting the touchless operation of the disinfector 100.

Figure 12B:
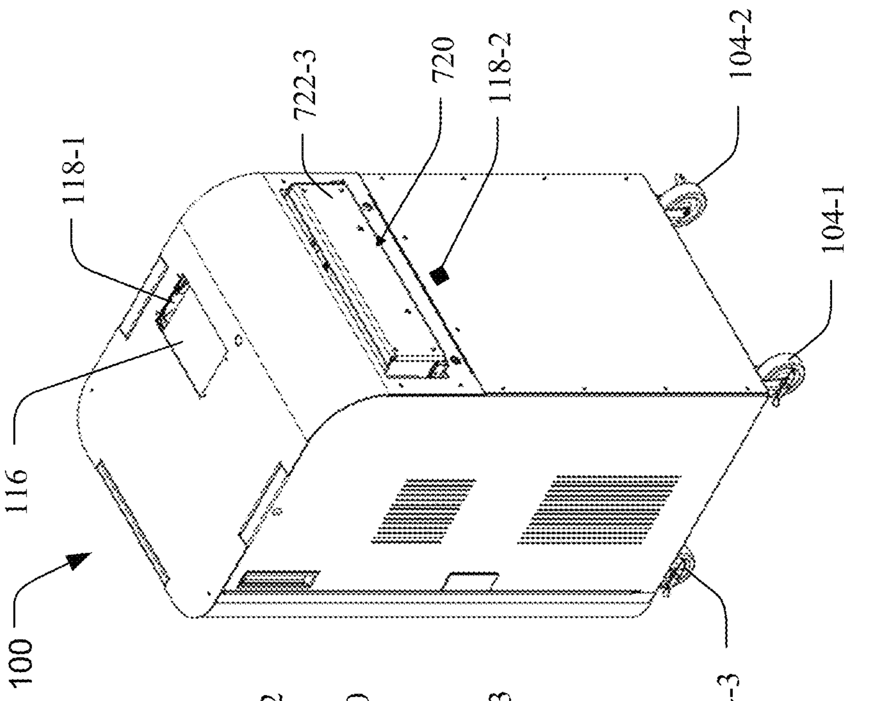
FIG. 12B is a front isometric view of the UV disinfector of FIG. 1 including the disinfection container of FIG. 12A, according to an embodiment of the present disclosure.
Figure 12A:
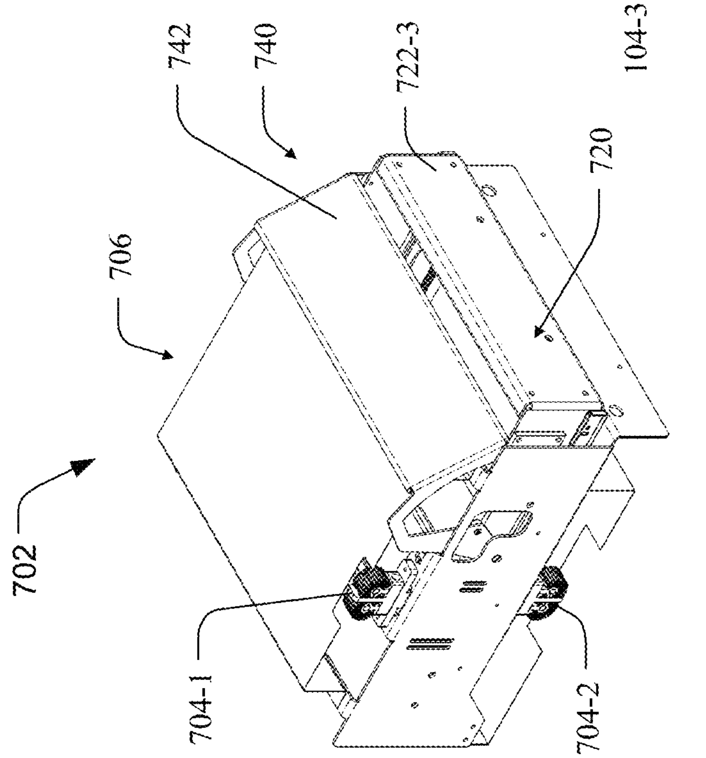
FIG. 12A is a front isometric view of the disinfection container of FIG. 7 including a fully-open barrier and a partially-extended tray, according to an embodiment of the present disclosure.
Figure 12D:
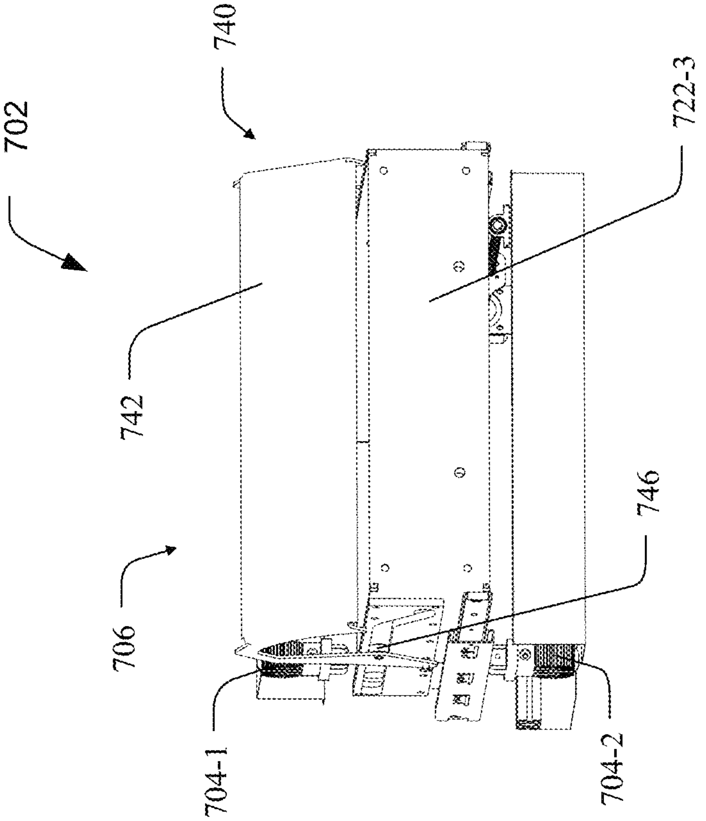
FIG. 12D is a front perspective view of the disinfection container of FIG. 12A, according to an embodiment of the present disclosure.
Figure 12C:
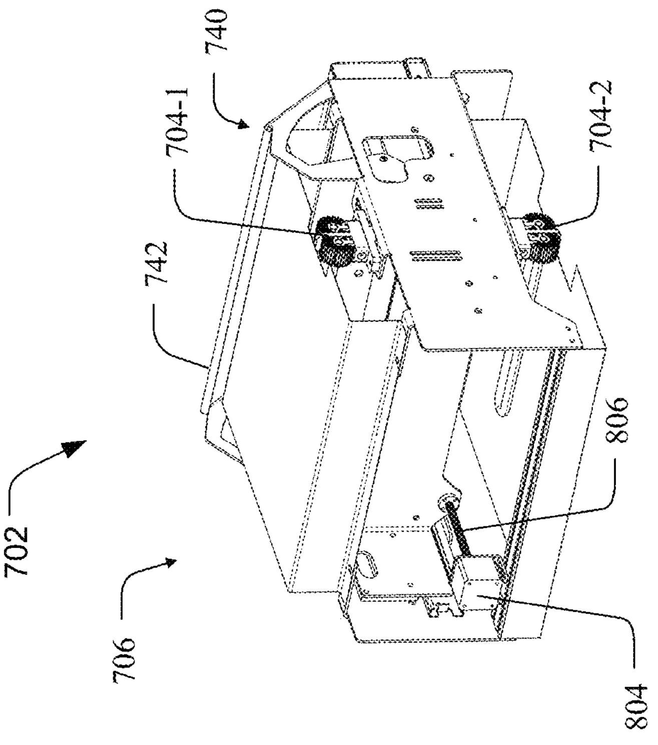
FIG. 12C is a rear isometric view of the disinfection container of FIG. 12A, according to an embodiment of the present disclosure.

As illustrated in FIG. 12C, the motor 804 may continue to drive the tray 720 forward or outward until the tray 720 is in the extended position relative to the support frame 706, as indicated by the rear sensor 118-3. As the tray 720 moves forward (FIG. 12A), the front cover 742 or the barrier 740 may pivot to the open position for being positioned above the top plate 710. Accordingly, as illustrated in FIG. 12B, the barrier 740 may pivot to fully unblock the front opening 112 of the disinfector 100 and allow the tray 720 to extend outwards from the front opening 112 of the disinfector 100. In such open position, as shown in FIG. 12D, the cams may be fully engaged with the elongated portion 728-1 of the tracks for positioning the front cover 742 of the barrier 740 completely away from the moving path of the tray 720 outside the support frame 706 (FIG. 12A).

In some embodiments, the controller 222 may cease to drive the motor 804 to stop any motion of the tray 720 if the front sensor 118-2 sends a signal indicating a value '1' while the tray 720 may be transitioning into the extended position for positioning the tray 720 outside the disinfector 100. The value '1' from the front sensor 118-2 may indicate that the moving path of the tray 720 outside the disinfector 100 may not be available or clear up to the minimum distance to allow the tray 720 to move into the extended position without any obstructions. At this point, the controller 222 may trigger a backward/inward motion of the tray 720 to transition back to the non-extended or retracted position within the support frame 706 based on the front sensor 118-2 detecting such obstruction or motion. Additionally, or alternatively, the controller 222 may provide an indication (e.g., pulsating light, beep, vibration, etc.) for a user to clear up the moving path and provide the minimum distance for moving the tray 720 outside the cabinet 108 or the disinfector 100.

Figure 13B:
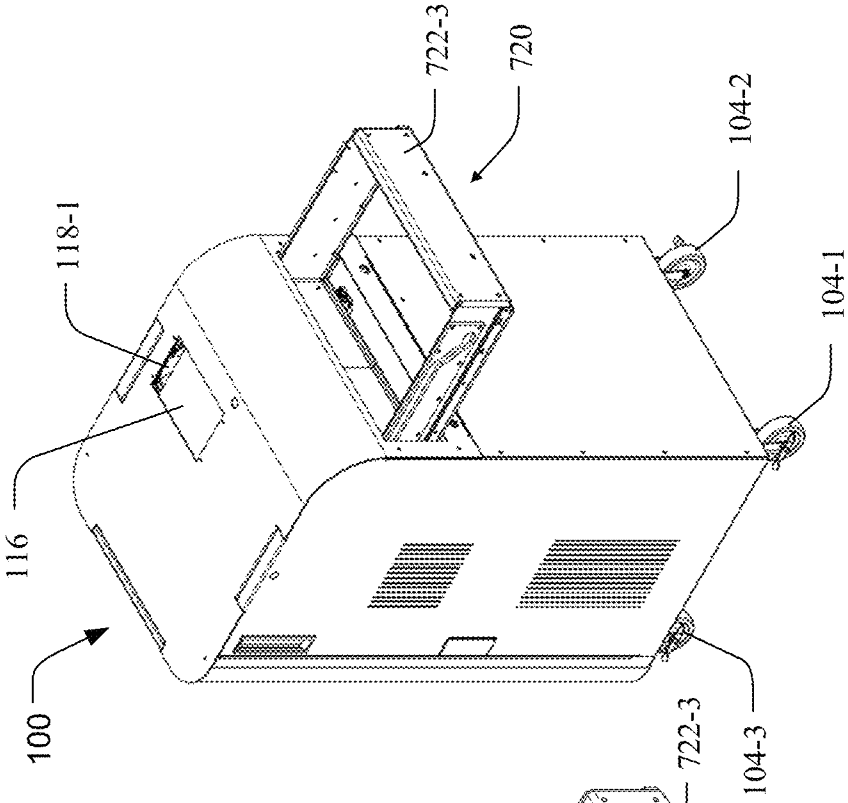
FIG. 13B is a front isometric view of the UV disinfector of FIG. 1 including the disinfection container of FIG. 13A, according to an embodiment of the present disclosure.
Figure 13A:
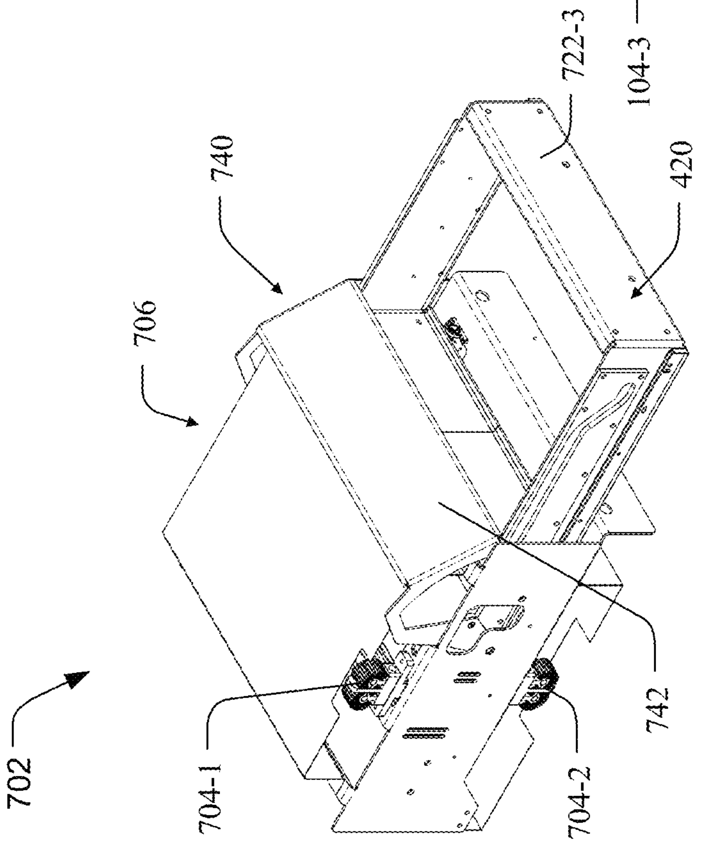
FIG. 13A is a front isometric view of the disinfection container of FIG. 7 including a fully-open barrier and a fully-extended tray, according to an embodiment of the present disclosure.
Figure 13D:
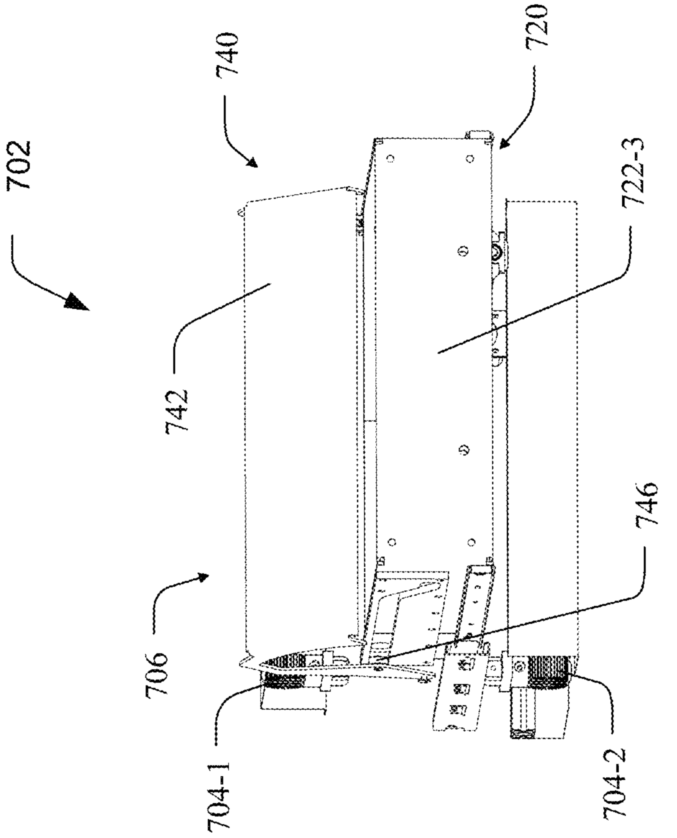
FIG. 13D is a front perspective view of the disinfection container of FIG. 13A, according to an embodiment of the present disclosure.
Figure 13C:
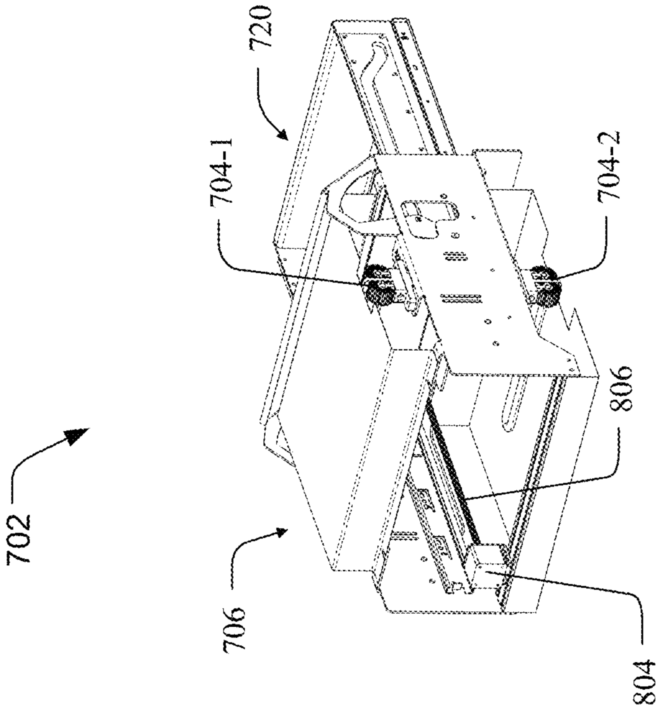
FIG. 13C is a rear isometric view of the disinfection container of FIG. 13A, according to an embodiment of the present disclosure.

As illustrated in FIG. 13C, the motor 804 may drive the tray 720 forward/outward from the disinfection container 702 to the extended position relative to the support frame 706. In the extended position of the tray 720 (FIG. 13A), the front cover 742, or the barrier 740, may be arranged in the open position and positioned above the top plate 710. Hence, as illustrated in FIG. 13B, the tray 720 may be substantially extended outside the front opening 112 of the disinfector 100. Additionally, the cams may engage with the elongated portion 728-1 of the tracks for positioning the front cover 742 of the barrier 740 away from the moving path of the tray 720 for arranging the tray 720 in the extended position substantially outside the disinfector 100 (FIG. 13B and FIG. 13D). In an embodiment, the controller 222 may be configured to keep the tray 720 in the extended position substantially outside the disinfector 100 until a signal indicating the value '1' may be received from at least one of the top sensor 118-1 and the front sensor 118-2. Other embodiments may include the controller 222 being configured to keep the tray 720 in the extended position for a predefined or dynamically defined duration (e.g., 15 seconds) at the end of which the controller 222 may automatically trigger the motor 804 for retracting the tray 720 to the non-extended or retracted position within the support frame 706 or the disinfection container 702.

Based on the tray 720 being in the extended position, an article, such as a portable article, may be placed on the base of the tray 720 by a user. Subsequently, the controller 222 may drive the tray 720 to move backward or inward for being positioned into the disinfection container 702. Such backward motion of the tray 720 may cause the cams to gradually transition from the elongated portion 728-1 to engage with the angled portion 728-2 of the tracks for positioning the tray 720 within the support frame 706 or the disinfection container 702. Upon engaging with the angled portion 728-2, the cams may gradually drive the barrier 740 to transition from the open position to the closed position for gradually blocking the front opening 112 of the disinfector 100. Accordingly, the front cover 742 of the barrier 740 may move from above the top plate 710 to position in front of the front wall 722-3 of the tray 720 and restrict the tray 720 within the support frame 706 or the disinfection container 702. In the closed position, the front cover 742 may also block the front opening 112 of the disinfector 100, thereby preventing access to any interior portion including the tray 720 within the cabinet 108 via the front opening 112 of the disinfector 100.

The rear sensor 118-3 may sense the tray 720 positioned in the non-extended or retracted position based on a predetermined position of the tray 720 relative to the support frame 706 and send a third signal, e.g., indicating a value '1,' to the controller 222. Accordingly, the controller 222 may activate the radiation units 704 to project germicidal light to disinfect the article placed in the tray 720. The radiation units 704 may be configured to project the germicidal light for a predetermined disinfection cycle based on a selected disinfection mode. The controller 222 may drive the radiation units 704 to irradiate timed pulses of the germicidal light, such as UV light, with each pulse having predefined characteristics such as energy, power, wavelength, and/or frequency. For example, the controller 222 may drive each of the radiation units 704, simultaneously or alternately, at a predefined or dynamically defined pulse frequency (e.g., 50 Hz) to emit an intended amount of energy per pulse. In another example, the controller 222 may drive the radiation units 704 at a combined pulse frequency of at least 20 Hz to emit a predefined amount of energy. In yet another example, the controller 222 may drive at least two of the radiation units 704 at different frequencies. For instance, the energy per pulse may range from 30 to 150 Joules and the pulse frequency may range from 10 Hz to 60 Hz. In some other examples, the controller 222 may trigger the radiation units 704 alternately to collectively emit the germicidal light on to the article, or the tray 720, in a pulsed manner. The controller 222 may toggle or switch from driving one radiation unit to another at a predefined or dynamically defined toggling rate to emit UV light within the disinfection cycle. In some instances, the toggling rate may be set based on the pulse frequency and/or the energy per pulse associated with one or more of the radiation units 704.

After the disinfection cycle is complete, the controller 222 may deactivate the radiation units 704 and trigger the motor 804 for driving the tray 720. The motor 804 may drive the tray 720 for transitioning from the non-extended or retracted position to the extended position outside the disinfector 100 to enable retrieval of the disinfected article from the tray 720. The rear sensor 118-3 may send the third signal indicating a value '0' indicating the tray 720 being positioned in the extended position to the controller 222. Other embodiments may include the controller 222 keeping the tray 720 in the non-extended or retracted position at the end of the disinfection cycle until the signal set (1, 0) may be received from the top sensor 118-1 and the front sensor 118-2 respectively. The top sensor 118-1 may send such first signal indicating the value '1' upon detecting an obstruction or motion, e.g., a user hand, within the predefined proximity thereof, thereby further automating the touchless operation of the disinfector 100 to access the tray 720 therewith to collect the disinfected article.

Various kinds, sizes, shapes, and materials of various components including those not necessarily depicted in the attached drawings may also be envisaged by invention(s) covered in the present disclosure. Notably, the figures and examples are not meant to limit the scope of the present disclosure to a single embodiment, but other embodiments are possible by way of interchange of some or all of the described or illustrated elements.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above-described embodiments, methods, and examples, but by all embodiments and methods within the scope and spirit of the invention(s).

We claim:

1. A method of disinfecting an article, the method comprising:
- providing a disinfection container inside a cabinet having an opening, the disinfection container including
  - an ultraviolet (UV) source,
  - a tray moveable between a first position outside the cabinet for placement and retrieval of an article in the tray and a second position within the disinfection container for disinfection of the article, and
  - a barrier pivotally coupled to the tray;
- moving the tray by a controller via an actuator, the tray upon moving
  - (i) outwards from the disinfection container, mechanically drives the barrier to move to a set position above or below the disinfection container within the cabinet and away from the opening for extending the tray to the first position via the opening and
  - (ii) towards the second position, mechanically drives the barrier to move within the cabinet and towards the opening for blocking the opening to prevent access to the tray in the second position through the opening,
- wherein the tray is moved towards
  - (i) the first position based on a first sensor input and completion of a disinfection cycle and
  - (ii) the second position based on a second sensor input and a set duration; and
- projecting UV light from the UV source on to the article in the second position of the tray until the disinfection cycle is complete.

2. The method of claim 1, wherein the step of moving further comprises pivoting the barrier (i) upwards when the tray is moved outwards from the disinfection container and (ii) downwards when the tray is moved towards to the second position.

3. The method of claim 1, wherein the tray includes a base for supporting the article and walls surrounding the base, wherein the base is optically permeable to the UV light and the walls include one or more reflectors.

4. The method of claim 1, wherein the UV source projects pulsed UV light.

5. The method of claim 1, wherein the step of projecting further comprises operating the UV source along with an additional UV source, wherein the UV source and the additional UV source are triggered alternately by the controller to collectively emit UV light in a pulsed manner on to the article.

6. The method of claim 1, wherein the step of moving further comprises receiving the first sensor input and the second sensor input from a proximity sensor, and wherein a predetermined distance moved by the tray towards the first position is managed by the controller based on a combination of inputs from at least two sensors including the proximity sensor.

7. A method of disinfecting an article, the method comprising:
- providing a cabinet enclosing a moveable tray and a barrier pivotally coupled to the tray, wherein the cabinet includes an opening configured for the tray to pass therethrough;
- moving, using a controller and upon completion of a set duration, the tray to transition between a first position outside the cabinet for placement and retrieval of an article in the tray and a second position within the cabinet for disinfection of the article, the tray upon being moved causing the barrier to move within the cabinet, wherein the tray moving (i) towards the first position mechanically drives the barrier to move to a set position above or below a container inside the cabinet and at least in-part unblock the opening and (ii) towards the second position mechanically drives the barrier to at least in-part block the opening; and projecting a germicide from a germicide source on to the article in the second position of the tray, wherein the germicide source includes an ultraviolet (UV) source and wherein the tray is moved towards the first position upon completion of a disinfection cycle.

8. The method of claim 7, wherein the germicide includes UV light.

9. The method of claim 7, wherein the germicide is projected in a pulsed manner.

10. The method of claim 7, wherein the tray includes an optically-permeable surface for receiving the article.

11. The method of claim 7, wherein the tray includes a reflector.

12. The method of claim 7, wherein the step of moving further comprises receiving, using the controller, an input from a proximity sensor for controlling a movement of the tray, and wherein a predetermined distance moved by the tray towards the first position is managed by the controller based on a combination of inputs from at least two sensors including the proximity sensor.

13. The method of claim 12, wherein the tray is moved towards the first position further based upon receiving a first input from the proximity sensor.

14. The method of claim 12, wherein the tray is moved towards the second position further based upon receiving a second input from the proximity sensor.

15. The method of claim 7, wherein the step of moving further comprises pivoting the barrier (i) upwards when the tray is moved towards the first position and (ii) downwards when the tray is moved towards to the second position.

16. The method of claim 7, wherein the step of projecting further comprises initiating the germicide source or the projection of germicide therefrom when the tray is located in the second position.

17. The method of claim 7, wherein the step of projecting further comprises operating the germicide source in combination with an additional UV source, wherein the germicide source and the additional UV source are triggered simultaneously or alternately by the controller.

18. The method of claim 7, wherein the tray is moveable within the container located inside the cabinet.

19. The method of claim 18, wherein the germicide source is attached to the container.

20. The method of claim 7, further comprising providing a mobile body configured for supporting the cabinet.

* * * * *